(12) United States Patent
Al-Ali et al.

(10) Patent No.: US 6,671,531 B2
(45) Date of Patent: Dec. 30, 2003

(54) SENSOR WRAP INCLUDING FOLDABLE APPLICATOR

(75) Inventors: Ammar Al-Ali, Tustin, CA (US); Eugene E. Mason, La Mirada, CA (US)

(73) Assignee: Masimo Corporation, Irvine, CA (US)

( * ) Notice: Subject to any disclaimer, the term of this patent is extended or adjusted under 35 U.S.C. 154(b) by 11 days.

(21) Appl. No.: 10/020,664

(22) Filed: Dec. 11, 2001

(65) Prior Publication Data
US 2002/0045807 A1 Apr. 18, 2002

Related U.S. Application Data

(63) Continuation-in-part of application No. 09/456,666, filed on Dec. 9, 1999, now Pat. No. 6,377,829.
(60) Provisional application No. 60/324,873, filed on Sep. 25, 2001, and provisional application No. 60/306,635, filed on Jul. 18, 2001.

(51) Int. Cl.[7] .................................................. A61B 5/00
(52) U.S. Cl. ...................................... 600/344; 600/323
(58) Field of Search ................................ 600/309–310, 600/322–323, 344; 356/39–42

(56) References Cited

U.S. PATENT DOCUMENTS

| 4,621,643 A | 11/1986 | New, Jr. et al. |
| 4,865,038 A | 9/1989 | Rich et al. |
| 5,090,410 A | 2/1992 | Saper et al. |
| 5,158,323 A | 10/1992 | Yamamoto et al. |

(List continued on next page.)

FOREIGN PATENT DOCUMENTS

| EP | 0 313 238 A2 | 10/1988 |
| WO | WO 01/41634 A2 | 6/2001 |

OTHER PUBLICATIONS

MSP Industry Alert, "Masimo To Introduce NR7 At ASA", pp. 18, 19, and the front and back cover, vol. 3, No. 3, Fall 2001.

(List continued on next page.)

*Primary Examiner*—Eric F. Winakur
*Assistant Examiner*—Matthew Kremer
(74) *Attorney, Agent, or Firm*—Knobbe, Martens, Olson & Bear LLP.

(57) ABSTRACT

A sensor wrap including a foldable applicator which substantially and removably secures sensor elements within the sensor wrap before application of the sensor wrap to a measurement site. The sensor wrap may advantageously include disposable tape layers including an information element, a breakable conductor, or both.

39 Claims, 23 Drawing Sheets

U.S. PATENT DOCUMENTS

| | | | |
|---|---|---|---|
| 5,170,786 A | | 12/1992 | Thomas et al. |
| 5,209,230 A | | 5/1993 | Swedlow et al. |
| 5,638,818 A | | 6/1997 | Diab et al. |
| 5,660,567 A | | 8/1997 | Nierlich et al. |
| 5,673,693 A | | 10/1997 | Solenberger |
| 5,678,544 A | | 10/1997 | DeLonzor et al. |
| 5,758,644 A | | 6/1998 | Diab et al. |
| 5,817,008 A | * | 10/1998 | Rafert et al. ............ 600/323 |
| 5,919,133 A | | 7/1999 | Taylor et al. |
| 5,995,855 A | | 11/1999 | Kiani et al. |
| 5,999,834 A | | 12/1999 | Wang et al. |
| 6,014,576 A | | 1/2000 | Raley |
| 6,061,584 A | | 5/2000 | Lovejoy et al. |
| 6,256,523 B1 | | 7/2001 | Diab et al. |

OTHER PUBLICATIONS http://www.masimo.com.htm, "System Overview & Performance", 2 pages, reviewed on Sep. 17, 1999.

http://www.masimo.com/pandt.htm, "Products & Technology", 1 page, reviewed on Sep. 17, 1999.

http://www.masimo.co./cables.htm, "Patient Cables", 1 page, review on Sep. 17, 1999.

http:// www.masimo.com/adt.htm, "Inop adt—Adult Disposable Digit Sensor", 1 page, reviewed on Sep. 17, 1999.

http://www.mrequipment.com/products/pulse_oximetry.htm, "MR Equipment Magnetic Resonance Equipment Corporation, Pulse Oximetry in MRI Model 3500 Oximeter", 2 pages, reviewed on Sep. 17, 1999.

http://www.mrequipment.com/products/oximetry_patient mntrg.htm, "MR Equipment Magnetic Resonance Equipment Corporation, MR–Compatible High–Performance Optical Fiber Sensors, Pulse Oximetry Sensors for MRI Fiber Optic Sensors for use with MR–Compatible Pulse Oximeter", 2 pages, reviewed on Sep. 17, 1999.

Masimo Corporation, "Discrete Saturation Transform Example", reviewed on Sep. 17, 1999.

* cited by examiner

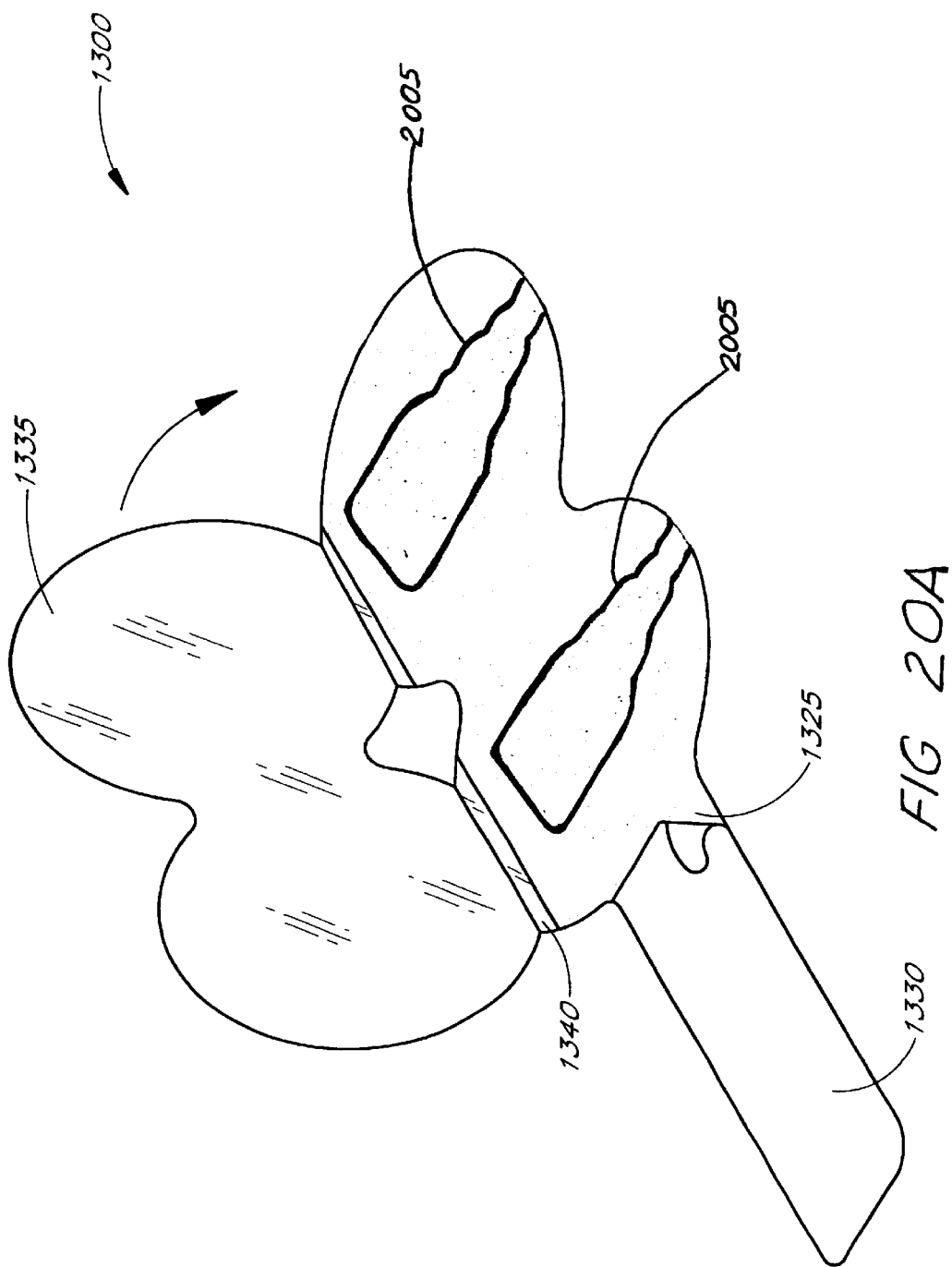

SENSOR WRAP INCLUDING FOLDABLE APPLICATOR

BACKGROUND OF THE INVENTION

REFERENCE TO RELATED APPLICATIONS

The present application is a continuation-in-part of U.S. patent application Ser. No. 09/456,666, filed Dec. 9, 1999, Now U.S. Pat. No. 6,377,829, entitled "RESPOSABLE PULSE OXIMETRY SENSOR," and claims priority benefit under 35 U.S.C. §120 to the same. Moreover, the present application claims priority benefit under 35 U.S.C. § 119(e) from U.S. Provisional Application No. 60/306,635, filed Jul. 18, 2001, entitled "SENSOR WRAP INCLUDING FOLDABLE APPLICATOR," and U.S. Provisional Application No. 60/324,873, filed Sep. 25, 2001, entitled "SENSOR WRAP INCLUDING FOLDABLE APPLICATOR." The present application incorporates the foregoing disclosures herein by reference.

1) Field of the Invention

Embodiments of the present invention relate in general to sensor wraps for securing a sensor to a measurement site, and relate in particular to sensor wraps including foldable applicators for securing elements of the sensor within the wrap.

2) Description of the Related Art

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed oximetry, a study and measurement of the oxygen status of blood. One particular type of oximetry, pulse oximetry, is a widely accepted noninvasive procedure for measuring the oxygen saturation level of arterial blood, an indicator of the oxygen status of the blood. A pulse oximeter relies on a sensor attached to a patient in order to measure the blood oxygen saturation.

Conventionally, a pulse oximeter sensor has a red emitter, an infrared emitter, and a photodiode detector. The sensor is typically attached to a patient's finger, earlobe, or foot. For a finger, the sensor is configured so that the emitters project light through the outer tissue of the finger and into the blood vessels and capillaries contained inside. The photodiode is positioned at the opposite side of the finger to detect the emitted light as it emerges from the outer tissues of the finger. The photodiode generates a signal based on the emitted light and relays that signal to an oximeter. The oximeter determines blood oxygen saturation by computing the differential absorption by the arterial blood of the two wavelengths (red and infrared) emitted by the sensor.

Conventional sensors are either disposable or reusable. A disposable sensor is typically attached to the patient with an adhesive wrap, providing a secure contact between the patient's skin and the sensor components. A reusable sensor is typically a clip that is easily attached and removed, or reusable circuitry that employs a disposable attachment mechanism, such as an adhesive tape or bandage.

The disposable sensor has the advantage of superior performance due to conformance of the sensor to the skin and the rejection of ambient light. However, repeated removal and reattachment of the adhesive tape results in deterioration of the adhesive properties and tearing of the tape. Further, the tape eventually becomes soiled and is a potential source of cross-patient contamination. The disposable sensor must then be thrown away, wasting the long-lived emitters, photodiode and related circuitry.

On the other hand, the clip-type reusable sensor has the advantage of superior cost savings in that the reusable pulse sensor does not waste the long-lived and expensive sensor circuitry. However, as mentioned above, the clip-type reusable sensor does not conform as easily to differing patient skin shape, resulting in diminished sensitivity and increased ambient light.

Similar to the clip-type reusable sensor, the circuit-type reusable sensor advantageously does not waste the sensor circuitry. On the other hand, the circuit-type reusable sensor fails to provide quality control over the attachment mechanism. Much like the disposable sensors, the attachment mechanism for the circuit-type reusable sensor may become soiled or damaged, thereby leading to cross-patient contamination or improper attachment. Moreover, because the reusable circuit is severable from the attachment mechanism, operators are free to use attachment mechanisms that are either unsafe or improper with regard to a particular type of reusable circuitry.

Based on the foregoing, significant and costly drawbacks exist in conventional disposable and reusable oximetry sensors. Thus, a need exists for an oximetry sensor that incorporates the advantages found in the disposable and reusable sensors, without the respective disadvantages.

SUMMARY OF THE INVENTION

Accordingly, one aspect of the present invention is to provide a reusable/disposable (resposable) sensor including a disposable adhesive tape component that can be removed from other reusable sensor components. This hybrid sensor combines the longevity and associated cost advantages of the reusable sensor with the performance features of the disposable.

According to one embodiment, the disposable adhesive tape comprises a sensor wrap configured to properly position the reusable sensor components with respect to each other and a measurement site. According to one embodiment, the sensor wrap includes a foldable applicator for straightforwardly attaching the reusable sensor components to the sensor wrap.

In one embodiment of the resposable sensor, the disposable tape, or sensor wrap, includes an information element along with a mechanism for the electrical connection of the information element to the emitters. The information element provides an indication to an attached oximeter of various aspects of the sensor.

According to another embodiment, the information element provides an indication of the sensor type. According to yet another embodiment, the information element provides an indication of the operating characteristics of the sensor. In yet another embodiment, the information element provides security and quality control. For instance, the information element advantageously indicates that the sensor is from an authorized supplier.

According to yet another embodiment, the information element is advantageously located in the disposable portion and configured to be in communication with the reusable portion via a breakable conductor. The breakable conductor is also located within the disposable portion such that excessive wear of the disposable portion results in isolation of the information element, thereby indicating that the disposable portion should be replaced. Moreover, the information element may comprise one or more passive or active components, ranging from a single coding resistor to an active circuit, such as a transistor network, a memory device, or a central processing component.

Therefore, aspects of one embodiment of the sensor wrap include a sensor wrap for removably securing an emitter and a detector of a pulse oximetry sensor to a measurement site. The sensor wrap also comprises a center portion configured to position an emitter and a detector of a sensor and an elongated portion extending from the center portion and configured to removably secure the sensor wrap to a measurement site. Moreover, the wrap includes a foldable portion extending from the center portion and configured to fold over the emitter and the detector when the emitter and the detector are positioned within the center portion and before application of the sensor wrap to the measurement site, thereby removably securing the emitter and detector within the center portion.

Aspects of another embodiment of the sensor wrap include a sensor wrap including a foldable tape for positioning elements of a sensor within the sensor wrap before application of the sensor wrap to a measurement site, thereby properly positioning the elements of a sensor with respect to one another, and eventually with respect to the measurement site. The sensor wrap also comprises a base tape comprising a positioning portion which receives at least one element of a sensor. The wrap also comprises a foldable tape attached to the base tape, wherein the foldable tape folds over the at least one element of the sensor before application of the sensor wrap to a measurement site, thereby removably securing the at least one element within the sensor wrap, and a fastener which removably secures the sensor wrap to the measurement site.

Aspects of another embodiment include a method of manufacturing the sensor wrap. The method comprises forming a base tape including at least one positioning element configured to position sensor elements on the base tape and forming a foldable tape including adhesive on at least one side and configured to fold over the sensor elements positioned on the base tape before application of the sensor wrap to a measurement site, thereby removably securing the sensor elements within the sensor wrap. The method also comprises connecting the foldable tape to the base tape and attaching release liners to exposed adhesive.

Aspects of another embodiment of using the sensor wrap include a method of attaching a sensor having reusable and disposable portions. The method comprises removing a release liner on a center portion of a disposable positioning tape, attaching reusable elements of a sensor to the center portion by aligning positioning elements of the sensor with positioning elements within the center portion. The method also comprises folding a foldable portion over the reusable elements of the sensor before application of the disposable positioning tape to a measurement site, thereby securing the reusable elements of the sensor within the center portion. In addition, the method comprises removing release liners from other portions of the disposable positioning tape, and affixing the disposable positioning tape, with the reusable sensor elements, to a measurement site.

BRIEF DESCRIPTION OF THE DRAWINGS

The present invention is described in more detail below in connection with the attached drawings, which are meant to illustrate and not limit the invention.

DETAILED DESCRIPTION OF THE PREFERRED EMBODIMENT

The configuration of an information element for an oximeter sensor and method of reading an information element with an attached oximeter is described in U.S. Pat. No. 5,758,644, assigned to the assignee of the current application, and incorporated by reference herein. Accordingly, the configuration and the implementation of an information element will be greatly summarized as follows.

Figure 1:
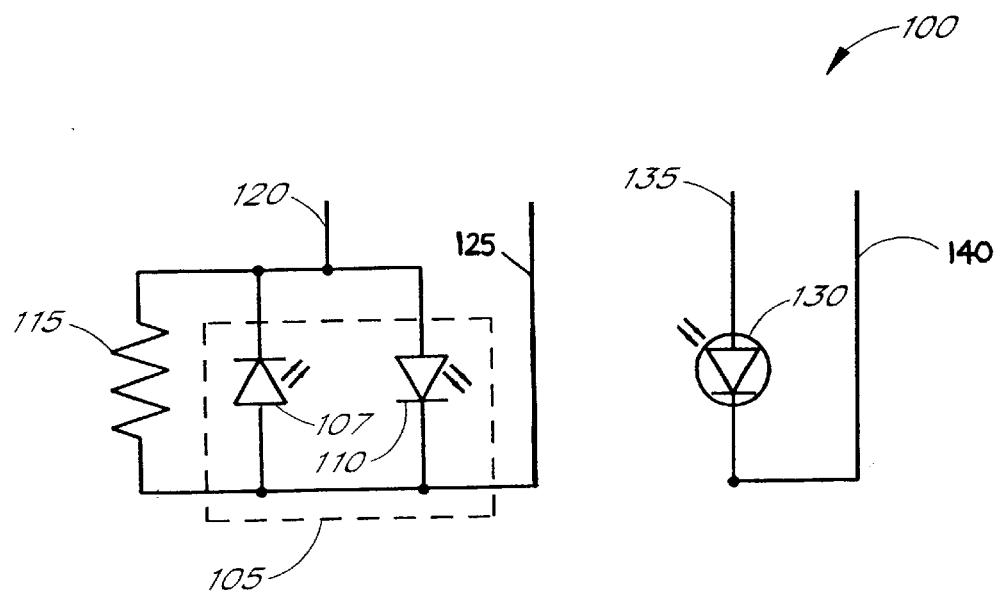
FIG. 1 illustrates a circuit diagram of a conventional disposable sensor including an information element.

FIG. 1 illustrates a conventional oximeter sensor circuit 100. The oximeter sensor circuit 100 includes an emitter 105 comprising a first LED 107 and a second LED 110. The oximeter sensor circuit further includes an information element comprising a resistor 115. The first LED 107, the second LED 110 and the resistor 115 are connected in parallel. The parallel connection has a common input electrical connection 120 and a first common return 125. The oximeter sensor circuit 100 also includes a photodetector 130 including an input electrical connection 135 connected to one end and including a second return 140 connected to the other end.

As mentioned, the resistor 115 may be provided as an information element that can be read by an attached oximeter. In order to read the resistor 115, the oximeter drives the oximeter sensor circuit 100 at a level where the emitter 105 draws effectively insignificant current. As is well understood in the art, the emitter 105 becomes active only if driven at a voltage above a threshold level. Thus, at this low level, significantly all of the current through the input electrical connection 120 flows through the resistor 115. By reducing the drive voltage across the input electrical connection 120 and the first common return 125 to a low enough level to not activate the emitter 105, the emitter 105 is effectively removed from the oximeter sensor circuit 100. Thus, the oximeter can determine the value of the resistor 115.

The value of the resistor 115 can be preselected to indicate, for example, the type of sensor (e.g., adult, pediatric, or neonatal), the operating wavelength, or other parameters about the sensor. The resistor 115 may also be utilized for security and quality control purposes. For example, the resistor 115 may be used to ensure that the oximeter sensor circuit 100 is configured properly for a given oximeter. For instance, the resistor 115 may be utilized to indicate that the oximeter sensor circuit 100 is from an authorized supplier.

Additionally, the elements of the oximeter sensor circuit 100 can advantageously be separated from one another. For example, the parallel connection between the emitter 105 and the resistor 115 can be spaced apart along the input electrical connection 120 and the first common return 125. For example, one embodiment can include the emitter 105 electrically connected between the input electrical connection 120 and the first common return 125 near the end thereof, while the resistor 115, still in parallel with the emitter 105, is electrically connected between the input and return 125 at a point closer to, or even as part of, the attached oximeter.

An information element other than the resistor 115 may also be utilized. The information element need not be a passive device. Coding information may also be provided through an active circuit, such as a transistor network, memory chip, or other identification device.

Furthermore, it will be understood by a skilled artisan that a number of different circuit configurations can be implemented that allow the oximeter sensor circuit 100 to include an information element. For example, the emitter 105 and the information element may each have individual electrical connections.

As mentioned above, the resistor 115 is preselected such that at low drive voltages, it is the only circuit element sensed by the oximeter. On the other hand, the resistor 115 can also be preselected be of a sufficiently high value that when the drive voltage rises to a level sufficient to drive the emitter 105, the resistor 115 is effectively removed from the oximeter sensor circuit 100. Thus, the resistor 115 does not affect normal operations of the emitter 105. In summary, an information element may form an integral part of the oximeter sensor circuit 100 by providing valuable information to the attached oximeter.

Figure 2A:
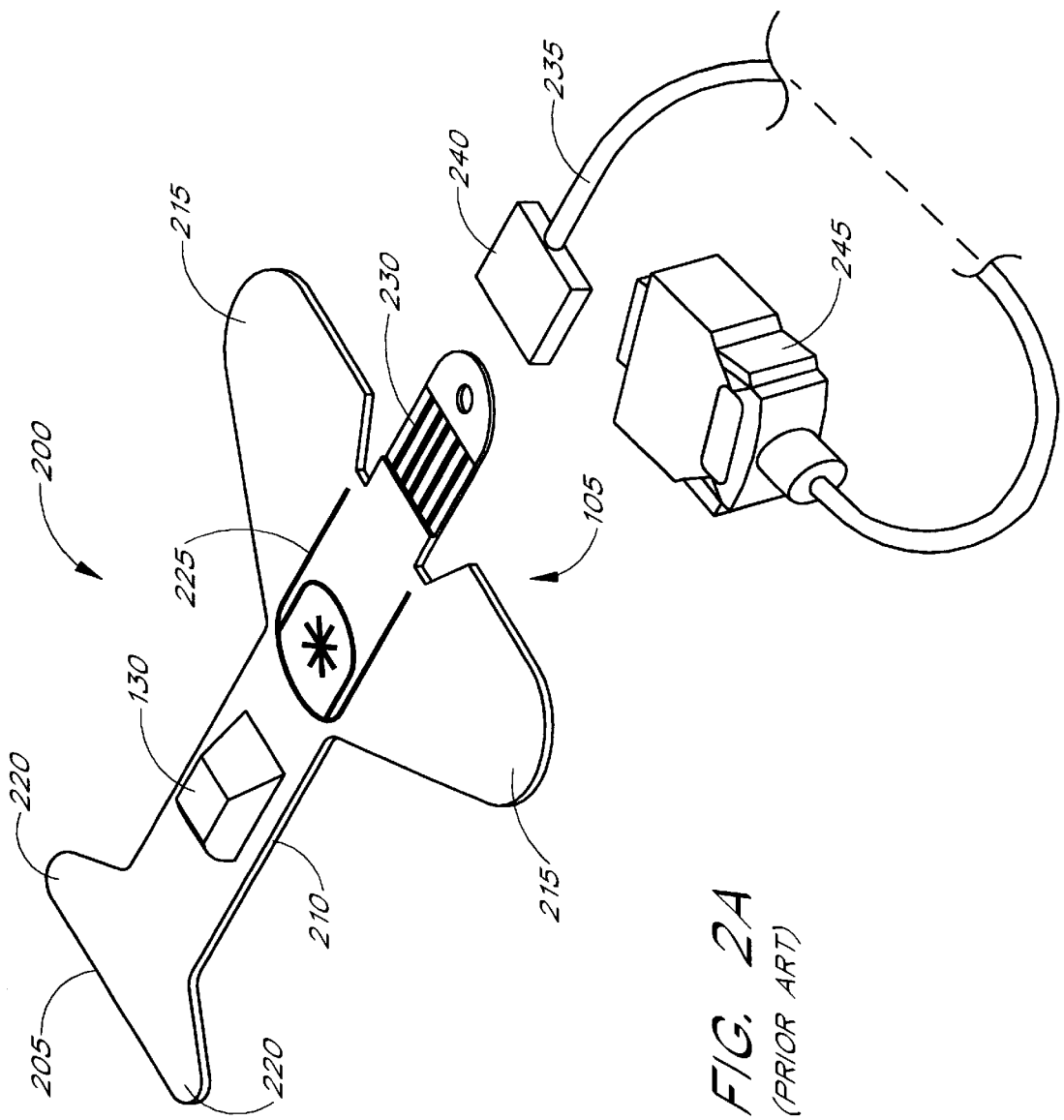
FIGS. 2A and 2B illustrate perspective views of the conventional disposable sensor.
Figure 2B:
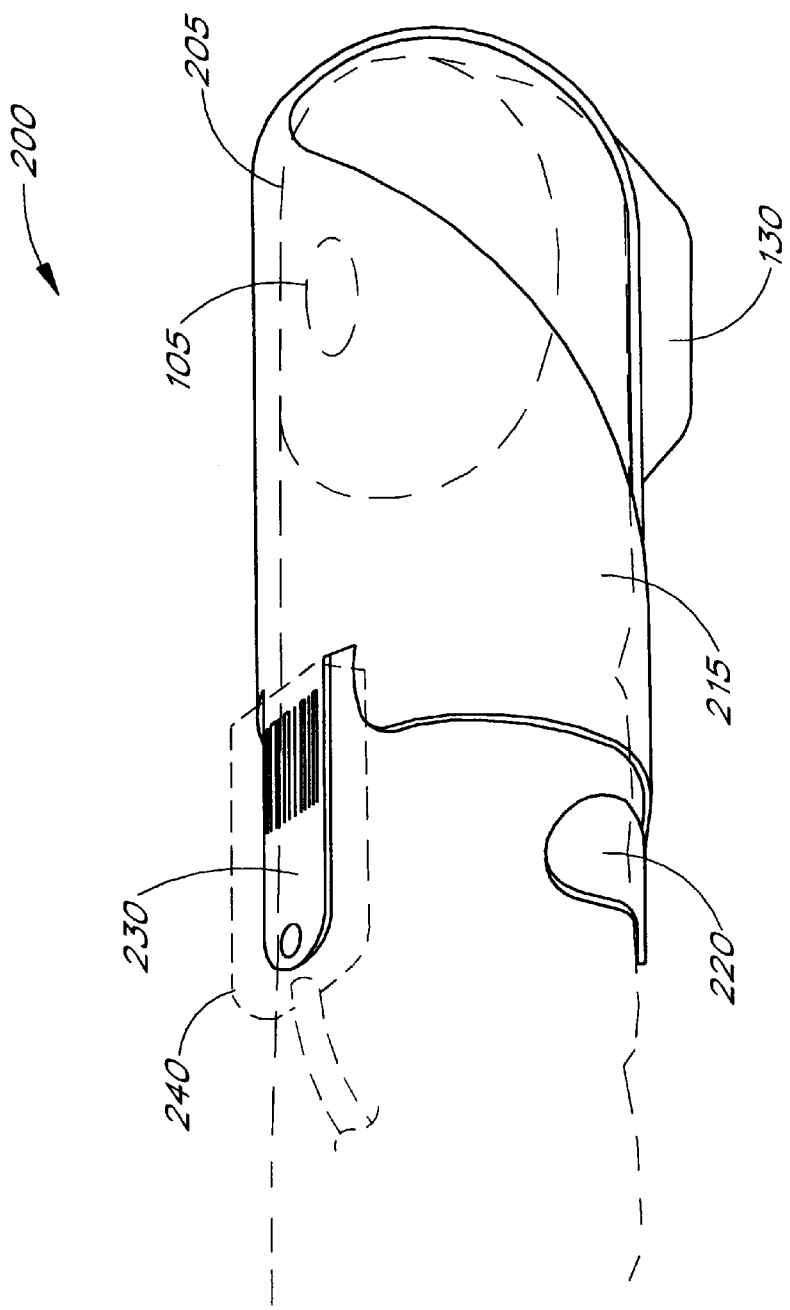

FIGS. 2A and 2B illustrate a conventional disposable sensor 200. The disposable sensor 200 includes an adhesive substrate 205 including an elongated center portion 210 with front and rear flaps, 215 and 220, extending outward from the elongated center portion 210. The adhesive substrate 205 may also have an image 225 superimposed on the adhesive substrate 205 so as to indicate proper use.

The elongated center portion 210 includes the oximeter sensor circuit 100 of FIG. 1. For example, the emitter 105 is housed on an underside of the elongated center portion 210 approximately beneath the superimposed image 225. Thus, as shown in FIG. 2A, the emitter 105 may be housed approximately beneath the asterisk superimposed on the image of a fingernail. On the other hand, the photodetector 130 is housed on the topside of the elongated center portion 210 in proximity with the rear flaps 220.

The elongated center portion 210 further includes an electrical connector 230 to drive the emitter 105 and to receive an output from the photodetector 130. The electrical connector 230 is preferably configured to attach to a connector cable 235 via a sensor connector 240. Also, the connector cable 235 attaches to or connects with an oximeter via an oximeter connector 245.

FIG. 2B illustrates an example of how the disposable sensor 200 wraps the front and rear flaps 215 and 220 around a finger such that the adhesive substrate 205 provides a secure contact between the patient's skin, the emitter 105 and the photodetector 130. FIG. 2B also illustrates an example of the sensor connector 240 (shown in broken lines) encompassing the electrical connector 230.

As shown in FIGS. 1–2B, the conventional disposable sensor 200 integrates the components of the conventional oximeter sensor circuit 100 such that disposal of the disposable sensor 200 includes disposal of the longer lasting, expensive circuitry found therein.

Figure 3:
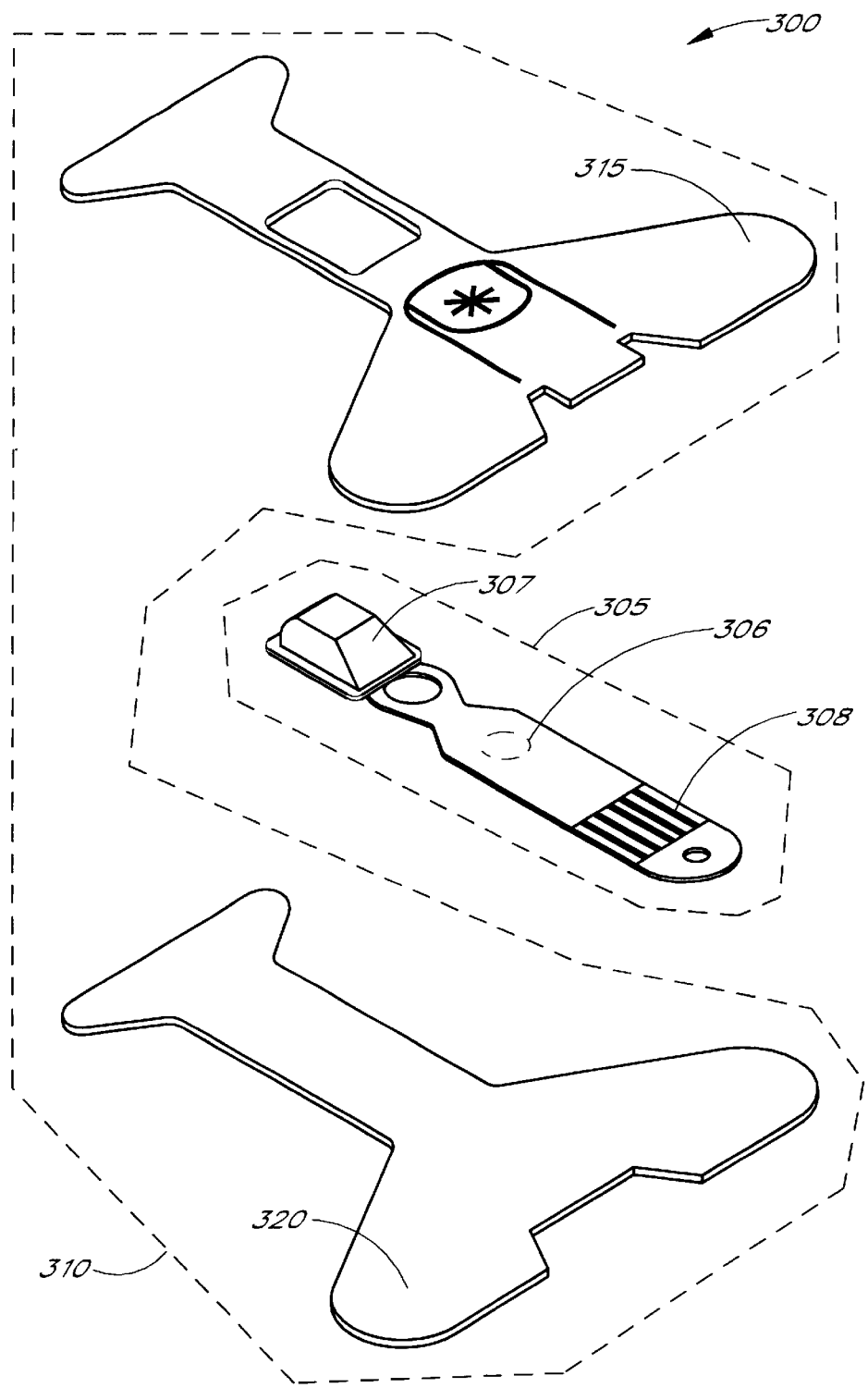
FIG. 3 illustrates an exploded view of a resposable sensor including two disposable tape layers, according to one embodiment of the invention.

FIG. 3 illustrates an exploded view of one embodiment of a resposable (reusable/disposable) sensor 300 according to the present invention. In this embodiment, the resposable sensor 300 includes a reusable portion 305 including an emitter 306, a photodetector 307 and an electrical connector 308. The resposable sensor also includes a disposable portion 310 including a face tape layer 315 and a clear base tape layer 320. As shown in FIG. 3, the disposable portion 310 attaches to the reusable portion 305 by sandwiching the reusable portion 305 between a face tape layer 315 and a clear base tape layer 320.

According to this embodiment, conventional adhesives or other attaching methodology may be used to removably attach the face tape layer 315 to the clear base tape layer 320. Furthermore, the adhesive properties associated with the base of the conventional disposable sensor 200 may be the same as the adhesive properties on the base of the clear base tape layer 320, as both portions are provided to attach to the patient's skin.

As mentioned, the disposable portion 310 removably attaches to the reusable portion 305 in, for example, a sandwich or layered style. After removably attaching the disposable portion 310 to the reusable portion 305, the resposable sensor 300 functions similar to the disposable sensor 200, i.e., the resposable sensor 300 wraps the flaps 215 around a patient's tissue such that the emitter 306 and the photodetector 307 align on opposite sides of the tissue. However, in contrast to the disposable sensor 200, the resposable sensor 300 provides for reuse of the reusable portion 305. For example, when the disposable portion 310 becomes contaminated, worn, or defective, rather than discarding the entire resposable sensor 300, the disposable portion 310 is removed such that the reusable portion 305 may be re-removably attached to a new disposable portion 310. The discarding of the disposable portion 310 completely avoids cross-contamination through the reuse of adhesive tapes between patients without wasting the more costly and longer lasting sensor circuitry of the reusable portion 305. Note that optional sterilization procedures may be advantageously performed on the reusable portion 305 before reattachment to either the new disposable portion 310 or to the patient, in order to further ensure patient safety.

Figure 4:
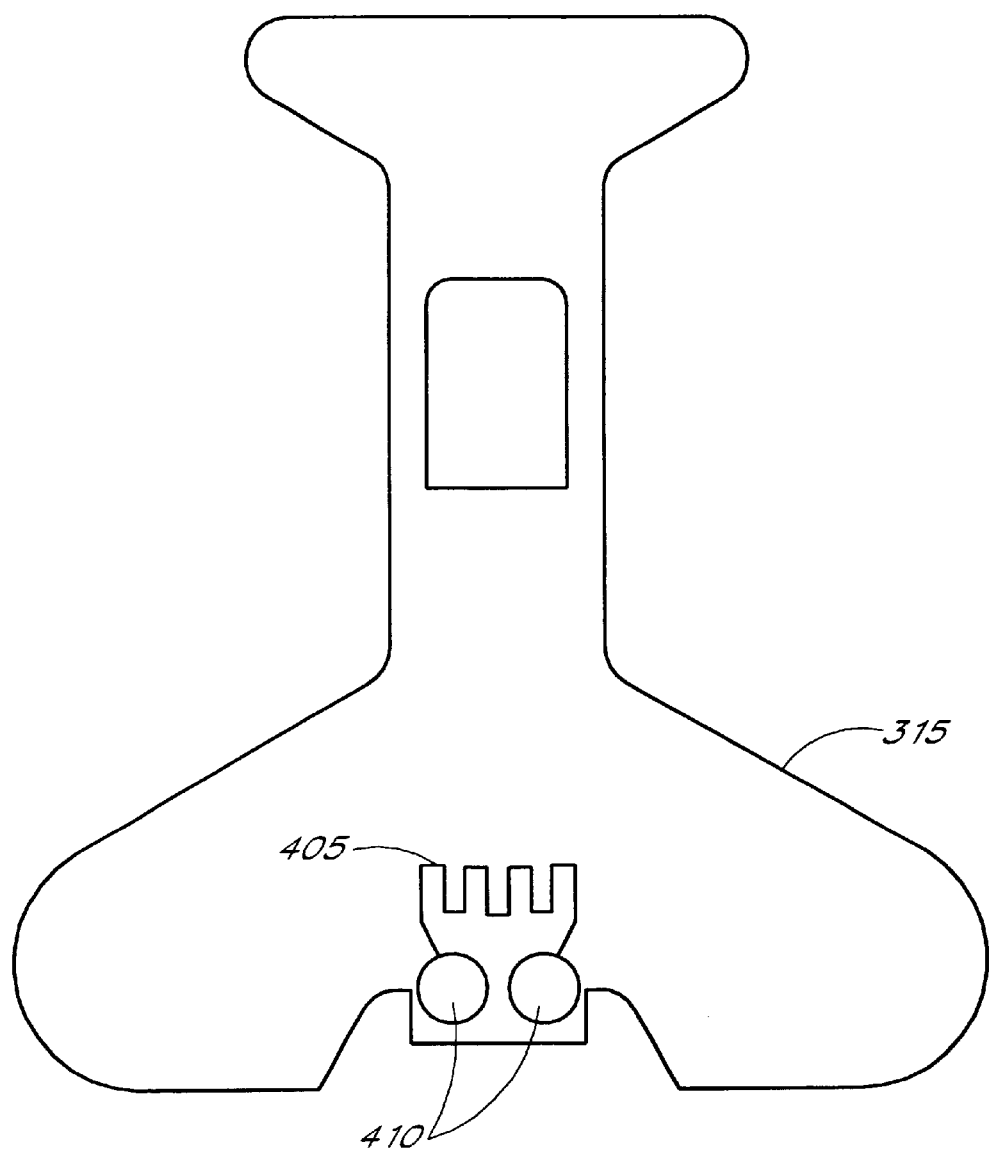
FIG. 4 illustrates a top view of one of the disposable tape layers of FIG. 3 incorporating an information element.

FIG. 4 illustrates a top view of an embodiment of the face tape layer 315 of the disposable portion 310 of the resposable sensor 300. According to this embodiment, the face tape layer 315 further includes an information element 405 as an integral part of the face tape layer 315. In this embodiment, the information element 405 is a resistive element made by depositing a conductive ink trace including a predetermined length and width. As is known in the art, the length, width and conductivity of the conductive ink trace determines the resistance of the resistive element. The information element 405 is deposited between contacts 410 that are also implemented with conductive ink. From the disclosure herein, a skilled artisan will understand that a variety of methods can be used for mating the contacts 410 with the electrical circuitry of the reusable portion 305. For example, the contacts 410 may advantageously physically touch the leads or the electrical connector 308 such that the reusable portion 305 is electrically configured to include the information element 405. Such a configuration employs the oximeter sensor circuit 100 of FIG. 1, including elements thereof distributed in both the reusable portion 305 and the disposable portion 310 of the resposable sensor 300.

In the foregoing embodiment, the disposable portion 310 comprises the information element 405 along with the face tape layer 315 and the clear base layer 320. As mentioned, the disposable portion 310 is removably attached to the reusable portion 305 and is employed in a similar manner as the disposable sensor 200. In contrast to the disposable sensor 200, when the disposable portion 310 of the resposable sensor 300 becomes worn, the disposable portion 310 and the information element 405 are discarded and the reusable portion 305 is saved. By discarding the information element, the attached oximeter can perform quality control. For example, if the reusable portion 305 is reattached to a patient using either a simple adhesive or any other non-authorized disposable mechanism, the resposable sensor 300 will not include the information element 405. As mentioned above, an attached oximeter can recognize the absence of the information element 405 and create an appropriate response indicating inappropriate use of the reusable portion 305 of the resposable sensor 300.

Figure 5:
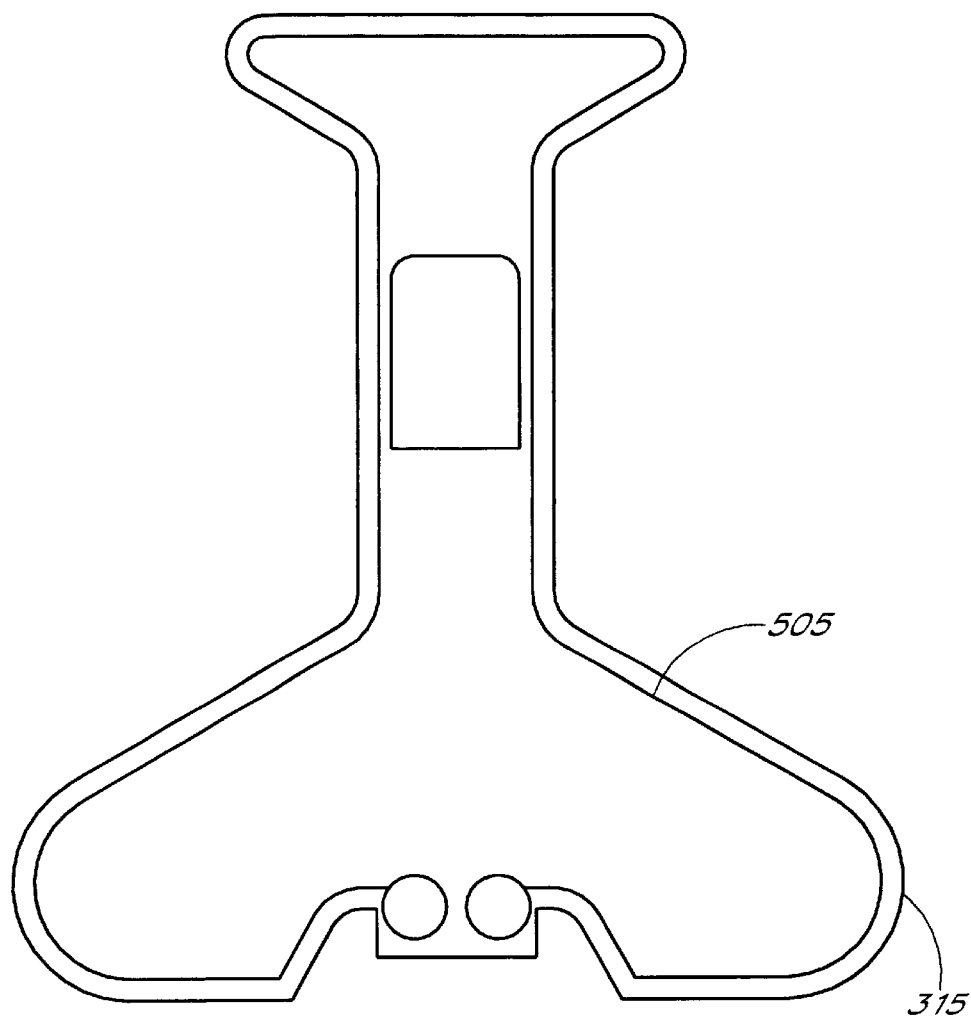
FIG. 5 illustrates a top view of one of the disposable tape layers of FIG. 3 incorporating a breakable conductor.
Figure 6A:
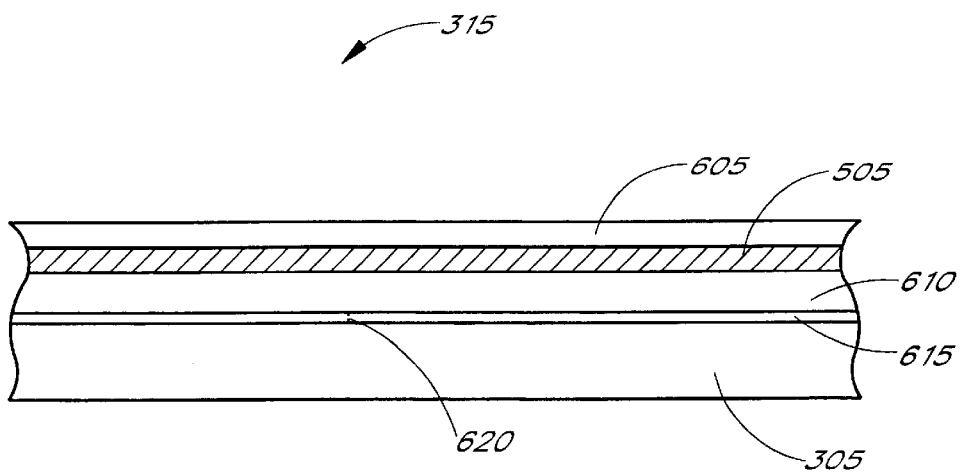
FIGS. 6A and 6B illustrate cross-sectional views of a portion of the disposable tape layer of FIG. 5.
Figure 6B:
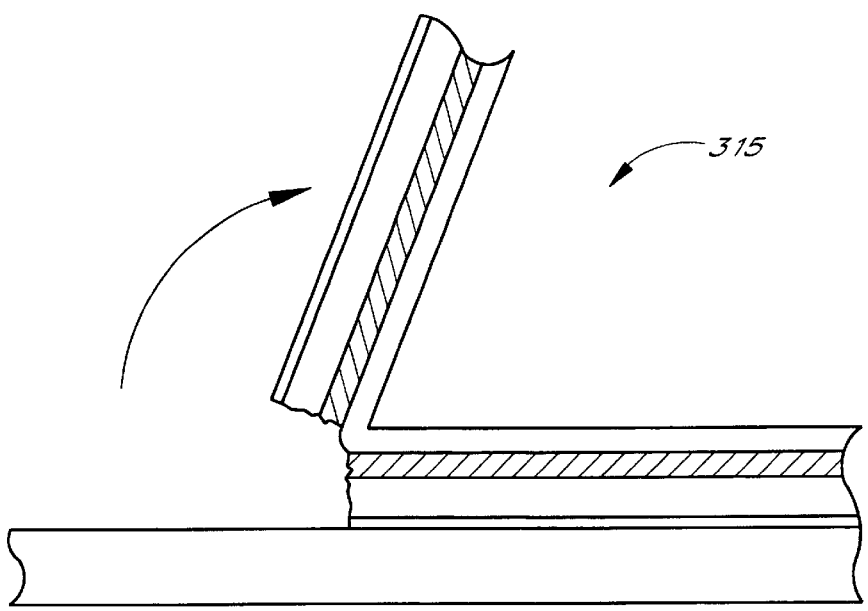

FIG. 5 illustrates a top view of yet another embodiment of the face tape layer 315 of the disposable portion 310 of the resposable sensor 300. In this embodiment, the face tape layer 315 includes a breakable conductor 505 comprising a conductive ink trace located approximately along the periphery of the face tape layer 315. This location ensures that a tear along the periphery of the face tape layer 315 results in a tear, or electrical discontinuity, in the breakable conductor 505. For example, FIGS. 6A and 6B illustrate the face tape layer 315 in which the breakable conductor 505 is layered between a tape stock 605 and a tape base 610. The reusable portion 305 of the resposable sensor 300 then attaches to the tape base 610 through a pressure sensitive adhesive (PSA) 615. The PSA 615, the conductor 505 and the tape base 610 include a score 620 such that multiple attachment and removal of the resposable sensor 300 will result in a peripheral tear, or electrical discontinuity, in the breakable conductor 505, as illustrated in FIG. 6B.

Thus, like the information element 405, the breakable conductor 505 also provides security and quality control functions. In particular, repeated use of the disposable portion 310 of the resposable sensor 300 advantageously severs at least one part of the breakable conductor 505. An attached oximeter can detect such severance and initiate an appropriate notification to, for example, monitoring medical personnel. Providing security and quality control through a breakable conductor advantageously assists in controlling problems with patient contamination or improper attachment due to weakened adhesives.

Figure 7:
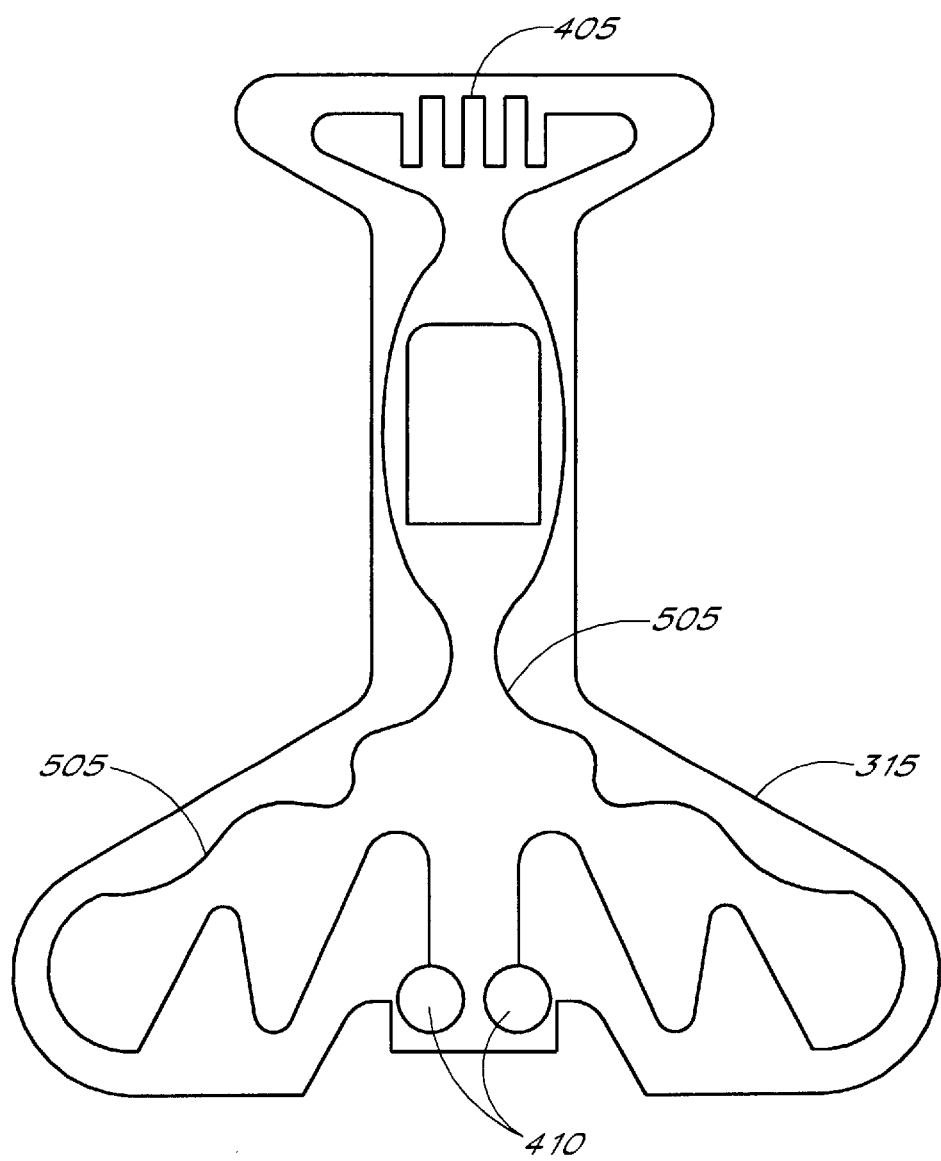
FIG. 7 illustrates a top view of one of the disposable tape layers of FIG. 3 incorporating the information element with a breakable conductor.

FIG. 7 illustrates yet another embodiment of the face tape layer 315. In this embodiment, the face tape layer 315 combines the breakable conductor 505 and the information element 405. In this embodiment, the breakable conductor 505 is printed in a serpentine pattern to further increase the probability of a discontinuity upon the tearing of any portion of the face tape layer 315. This combination of the information element 405 and the breakable conductor 505 advantageously adds significant safety features. For example, in this embodiment, the information element 405 is connected serially with the breakable conductor 505 and in parallel with the emitter 306 of the reusable portion 305. Therefore, any discontinuity or tear in the breakable conductor 505 separates the information element 405 from the circuitry of the reusable portion 305.

According to the foregoing embodiment, the attached oximeter receives an indication of both overuse and misuse of the resposable sensor 300. For example, overuse is detected through the tearing and breaking of the breakable conductor 505, thereby removing the information element 405 from the resposable sensor 300 circuitry. In addition, misuse through employment of disposable portions 310 from unauthorized vendors is detected through the absence of the information element 405. Moreover, misuse from purposeful shorting of the contacts 410 is detected by effectively removing the emitter 306 from the circuit, thereby rendering the resposable sensor 300 inoperative. Therefore, the resposable sensor 300 of this embodiment advantageously provides a multitude of problem indicators to the attached oximeter. By doing so, the resposable sensor 300 advantageously prevents the likelihood of contamination, adhesive failure, and misuse. The resposable sensor 300 also advantageously maintains the likelihood of quality control.

A skilled artisan will recognize that the concepts of FIGS. 3–7 may be combined in total or in part in a wide variety of devices. For example, either or both of the breakable conductor 505 and the information element 405 may advantageously be traced into the clear base tape layer 320 rather than into the face tape layer 315.

Figure 8A:
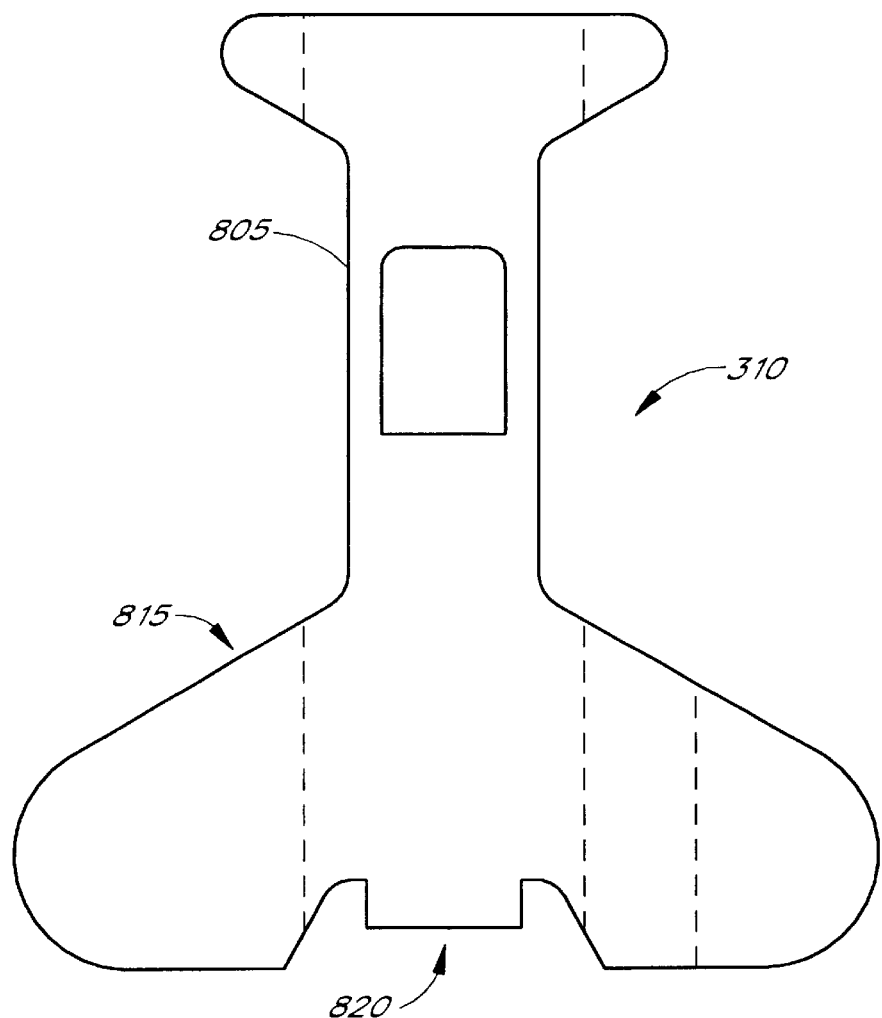
FIGS. 8A and 8B illustrate a top view and a side view, respectively, of one of the disposable layers of FIG. 3 configured as a fold-over tape.
Figure 8B:
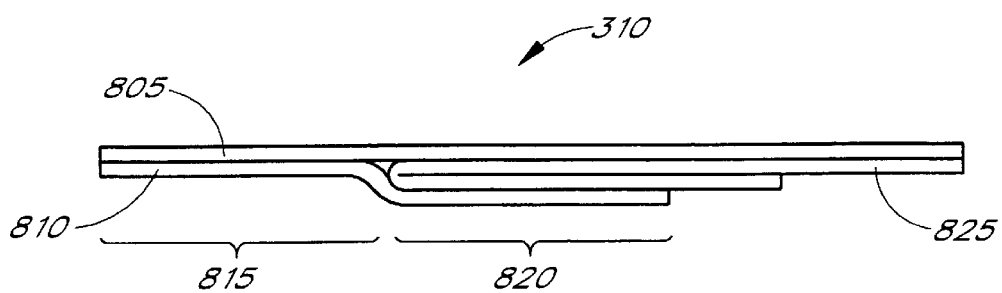

FIGS. 8A and 8B illustrate yet another embodiment of the disposable portion 310 of the resposable sensor 300 according to the present invention. As shown in this embodiment, the disposable portion 310 includes a face tape layer 805 and a clear base tape layer 810. According to this embodiment, the clear base tape layer 810 includes a preattached section 815 and a fold over section 820. The preattached section 815 attaches approximately one third of the face tape layer 805 to the clear base tape layer 810. On the other hand, the fold over section 820 forms a flap configured to create a cavity between the face tape layer 805 and the clear base tape layer 810. The cavity is configured to receive the reusable portion 305 of the resposable sensor 300. According to one embodiment, a release liner 825 fills the cavity and separates the face tape layer 805 from the clear base tape layer 810. When the release liner 825 is removed, newly exposed adhesive on the fold over section 820 and the face tape layer 805 removably attaches the reusable portion 305 between the face tape layer 805 and fold over section 820 of the clear base tape layer 810.

According to another embodiment, the cavity is so formed that adhesive is not needed. For example, the fold over section 820 may comprise resilient material that can form a friction fit relationship so as to fix the reusable portion 305 in an appropriate position relative to the disposable portion 310. On the other hand, the fold over section 820 may also comprise material including other than resilient or adhesive properties, but still allow for proper placement of the reusable portion 305 and disposable portion 310 on the patient. For example, hook-and-loop type materials like VELCRO® may be used.

It will be understood that a skilled artisan would recognize that the fold over embodiment of the responsible sensor 300 may employ the properties discussed in relation to FIGS. 3–7, such as the information element 405 and the breakable conductor 505.

Figure 9A:
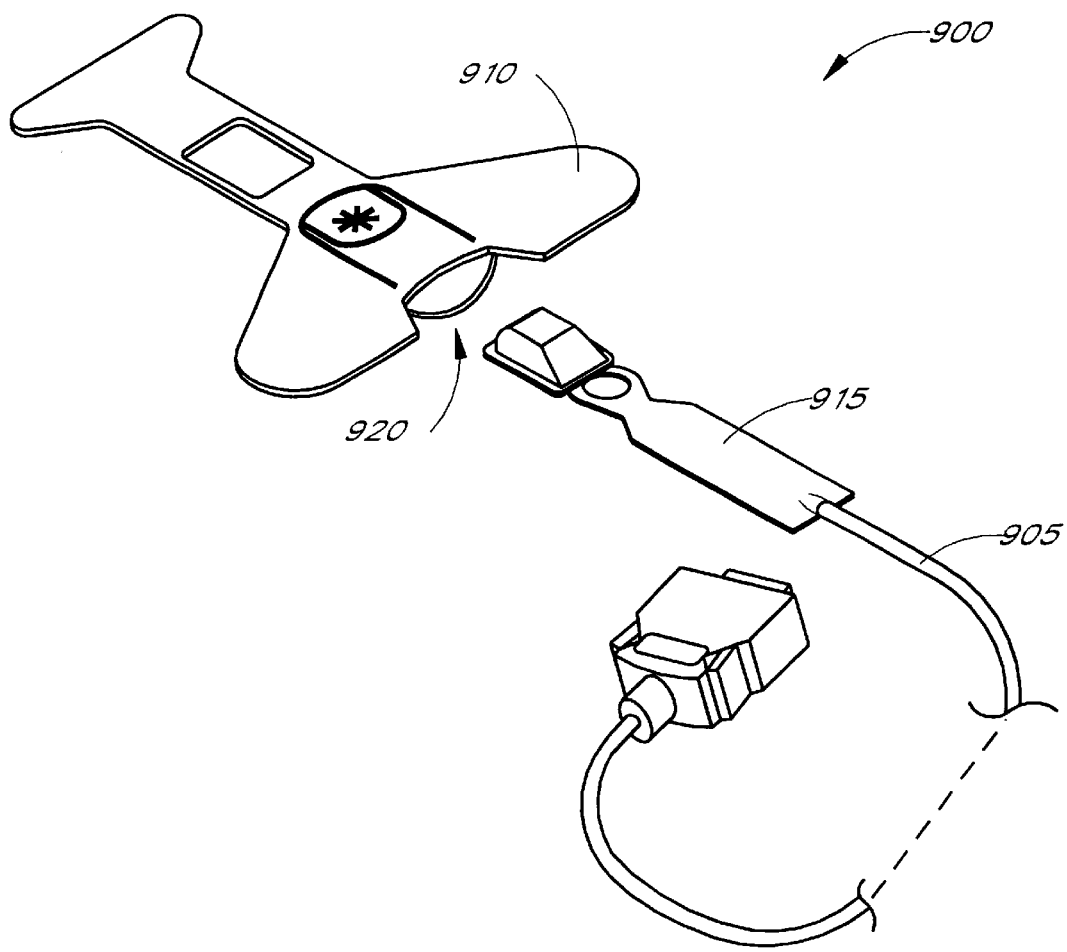
FIG. 9A illustrates a perspective view of a resposable sensor including a disposable portion configured as a tape sleeve and a reusable portion directly attached to a patient cable, according to another embodiment of the invention.

FIG. 9A illustrates an embodiment of a resposable sensor 900 integrated with an attached patient cable 905, according to another embodiment of the invention. In this embodiment, a disposable portion 910 is attached to a reusable portion 915 by removably inserting the reusable portion 915 into a tape envelope 920 formed in the disposable portion 910.

A skilled artisan will recognize that the disposable portion 910 may include the information element 405, the breakable conductor 505, or both. Inclusion of one or both of these electronic components in the resposable sensor 900 advantageously provides the security, quality control, and safety features described in the foregoing embodiments.

Figure 9B:
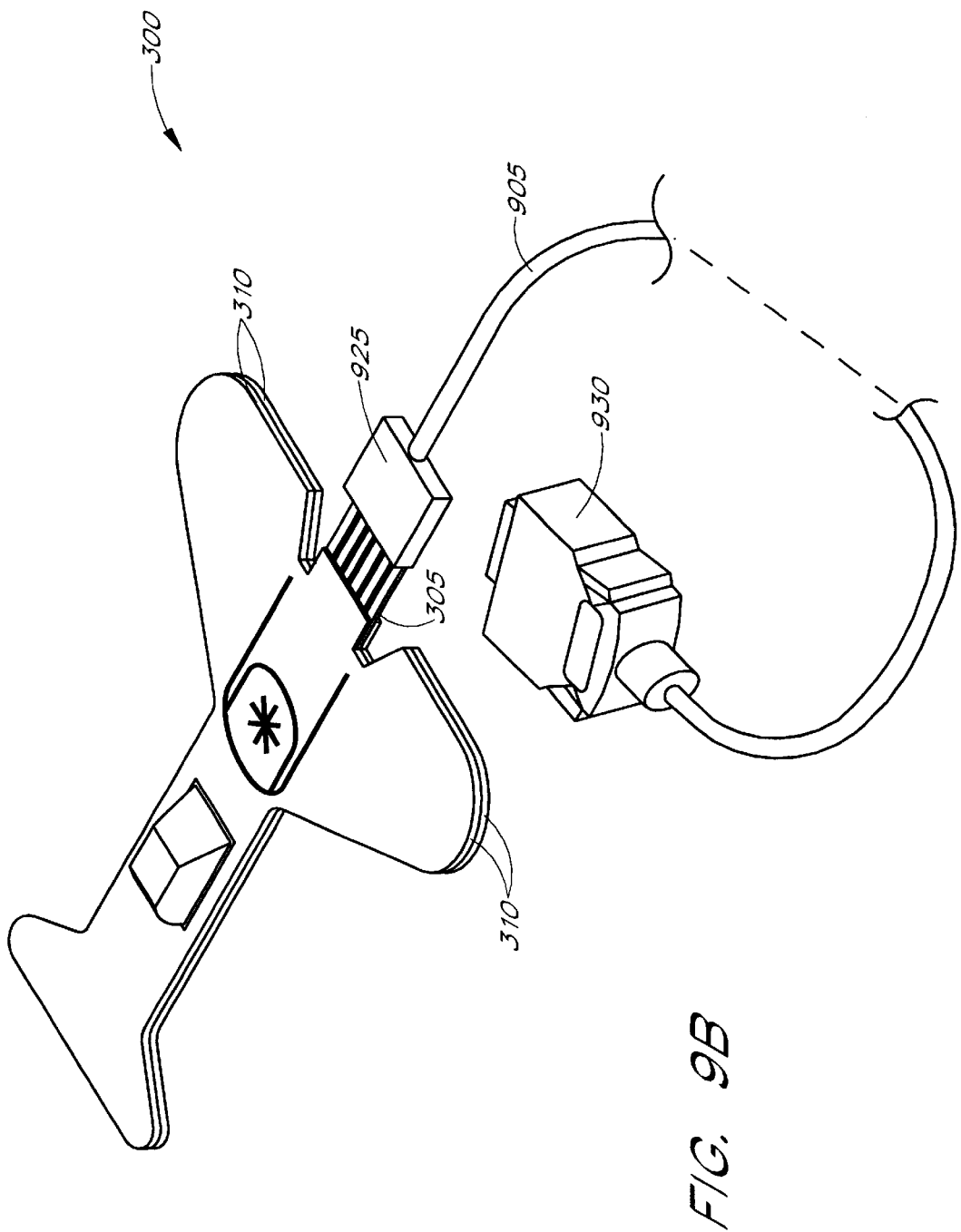
FIG. 9B illustrates a perspective view of a resposable sensor including a reusable portion removably attached to a patient cable, according to another embodiment of the invention.

FIG. 9B illustrates an embodiment of a resposable sensor 300 of FIG. 3, according to another embodiment of the invention. According to this embodiment, the resposable sensor 300 removably attaches to the patient cable 905 via a sensor connector 925. The patient cable 905 then attaches to an oximeter via an oximeter connector 930. Use of the sensor connector 925 enables the replacement of the reusable portion 305 of the resposable sensor 300 without replacement of the sensor connector 925 or the patient cable 905. In such an embodiment, the disposable portion 310 would follow a different, more frequent, replacement schedule than that of the reusable portion 305.

Figure 10:
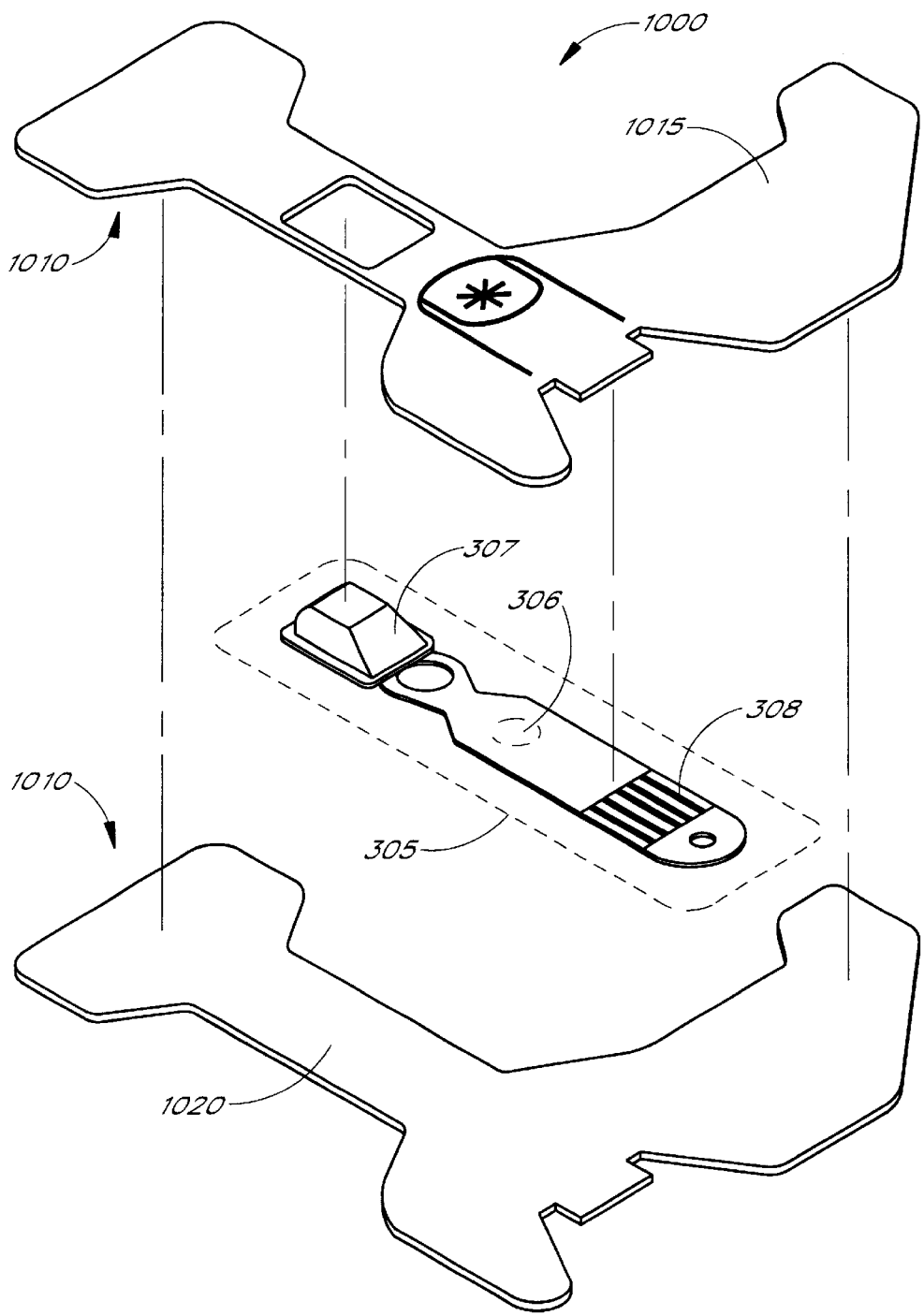
FIGS. 10–11 illustrate exploded views of a resposable sensor including two disposable tape layers, according to other embodiments of the invention.

FIG. 10 illustrates an exploded view of yet another embodiment of a resposable sensor 1000 including two disposable tape layers 1010. Similar to the resposable sensor 300 described with reference to FIG. 3, the resposable sensor 1000 includes various reusable components 305, including the emitter 306, the photodetector 307 and the electrical connector 308. Although the reusable components of the resposable sensor 1000 are illustrated in a similar fashion to that of the flex circuit described with reference to FIG. 3, a skilled artisan will recognize from the disclosure herein a wide number of reusable circuit configurations, including the emitter 306 and detector 307 connected to the electrical connector 308 by one or more flexible wires or the like.

The resposable sensor 1000 also includes the disposable portion 1010 including a face tape layer 1015 and a base tape layer 1020. As shown in FIG. 10, the disposable portion 1010 attaches to the reusable components 305 by sandwiching the reusable components 305 between the disposable tape layers 1015 and 1020. Similar to the tape layers disclosed with reference to FIG. 3, the disposable portion 1010 removably attaches to the reusable components 305 such that when the disposable portion 1010 becomes contaminated, worn, or defective, it can be discarded without wasting the reusable components.

As shown in FIG. 10, one embodiment of the disposable portion 1010 comprises a boot-like shape where the toe of the boot is configured to wrap around the measurement site, thereby substantially securing the sensor 1000 to the patient. However, a skilled artisan will recognize a wide number of shapes that advantageously secure the reusable components to differing types of measurement sites.

Figure 11:
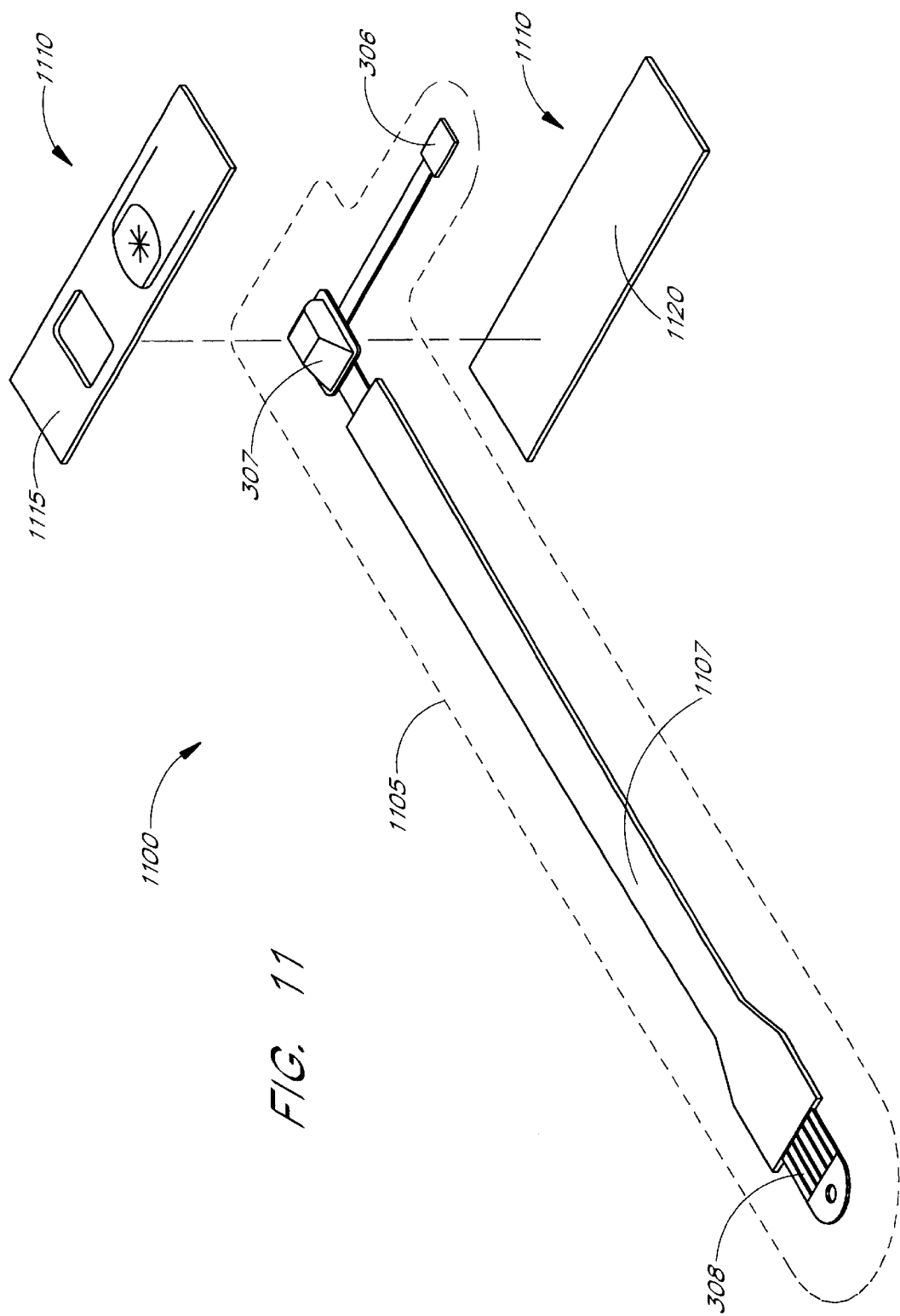

FIG. 11 illustrates an exploded view of yet another embodiment of a resposable sensor 1100 including reusable components 1105 and two disposable tape layers 1110. Similar to responsible sensor 1000 disclosed with reference to FIG. 10, the resposable sensor 1100 includes various reusable components 1105, including the emitter 306, the photodetector 307 and the electrical connector 308. Moreover, as shown in FIG. 11, the reusable components 1105 also include an elongated enclosed center portion 1107. According to one embodiment, the center portion 1107 encloses an electrical pathway, such as, for example, one or more wires, a flex circuit having one or more conductive paths, one or more conductive traces, or the like, in a preferably flexible housing, such as, for example, a reusable tape layer, plastic housing, cable, or the like. The center portion 1107 connects the emitter 306 and the photodetector 307 to the electrical connector 308. By employing the center portion 1107, the resposable sensor 1100 advantageously provides for removal of connection devices from the immediate area of the measurement site, thereby providing additional convenience in the placement of potentially multiple wires from multiple patient monitoring devices, including the oximeter.

The resposable sensor 1100 also includes a disposable portion 1110 including a face tape layer 1115 and a base tape layer 1120. As shown in FIG. 11, the disposable portion 1110 attaches to the reusable components 1105 by sandwiching at least some of the reusable components 1105 between the tape layers 1115 and 1120. Similar to the tape layers disclosed with reference to FIG. 3, the disposable portion 1110 removably attaches to at least some of the reusable components 1105 such that when the disposable portion 1110 becomes contaminated, worn, or defective, it can be discarded without wasting the reusable components.

As shown in FIG. 11, one embodiment of the disposable portion 1110 comprises a generally rectangular shape. According to one embodiment, the rectangular portion may have a length substantially shorter than that of the center portion 1107. According to one embodiment, the rectangular portion may have a length approximately one-third that of the center portion 1107. However, a skilled artisan will recognize from the disclosure herein, a wide number of shapes that advantageously secure portions of the reusable components 1105 to a measurement site. Moreover, a skilled artisan will recognize from the disclosure herein that the disposable portions of FIGS. 9A–11 may advantageously include the information element 405, the breakable conductor 505, or both. In addition, the information element 405 or the breakable conductor 505 may advantageously be incorporated in one or both of the disclosed tape layers for each sensor.

Although the foregoing invention has been described in terms of certain preferred embodiments, other embodiments will be apparent to those of ordinary skill in the art. For example, select aspects of FIGS. 3–11 may be combined. For example, the envelope configured disposable portion 910 of FIG. 9A may be combined with the reusable portion 305 of FIG. 3. Also, the reusable components of the various disclosed embodiments may advantageously directly connect to a patient cable 905 as illustrated in FIG. 9A, use the sensor connector 925 of FIG. 9B, or the like.

Figure 12:
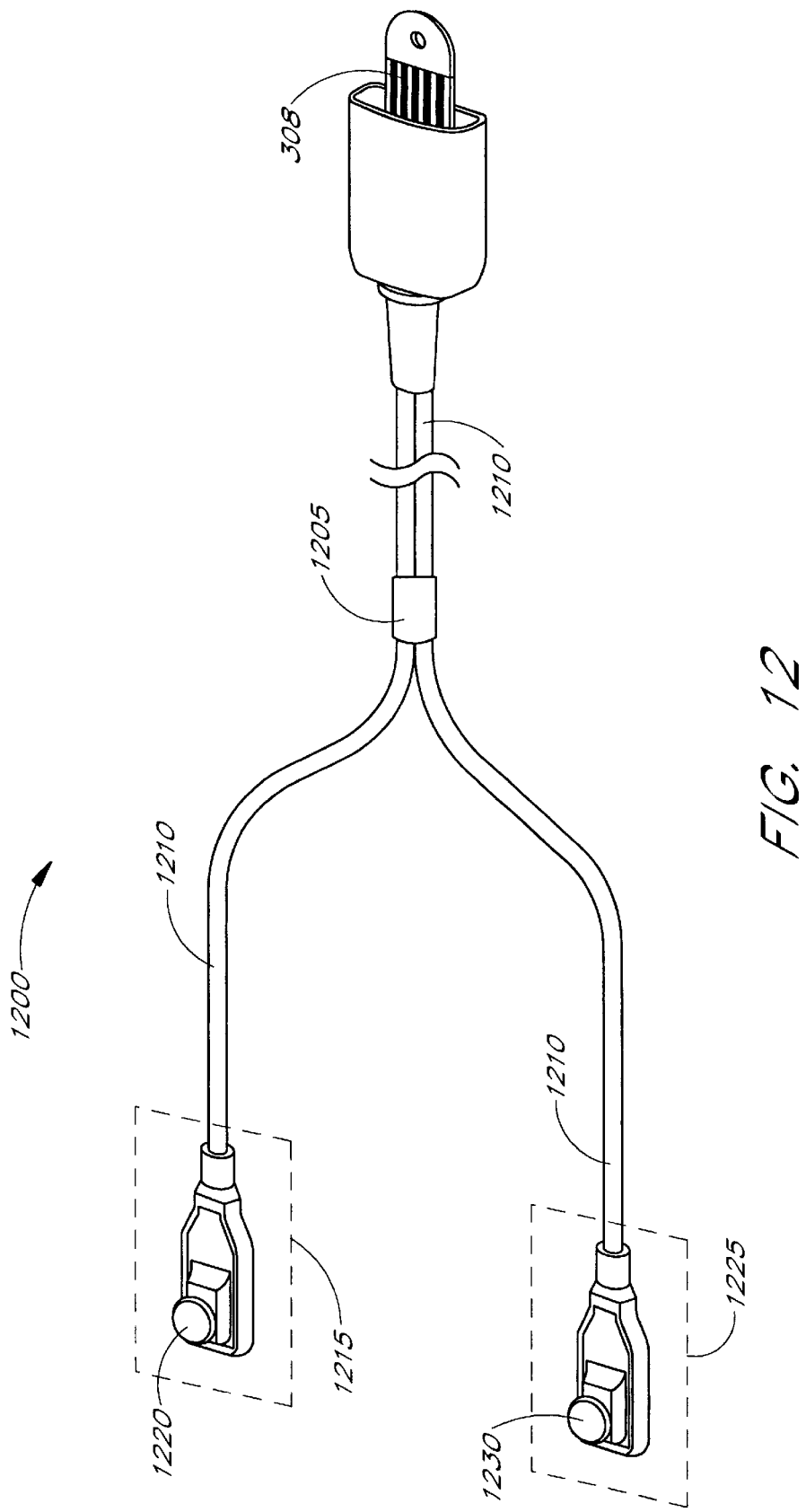
FIG. 12 illustrates a perspective view of a multisite sensor according to aspects of yet another embodiment of the invention.

FIG. 12 illustrates a perspective view of a multisite sensor 1200 according to aspects of yet another embodiment of the invention. As shown in FIG. 12, the multisite sensor 1200 includes the electrical connector 308, a neck 1205, elongated flexible wire 1210, sensor elements or portions 1215 and 1225, each including one positioning member 1220 and 1230, respectively. According to one embodiment, the electrical connector 308 of the multisite sensor 1200 is adapted to connect to the sensor connector 925 to establish electrical communication to and from the sensor elements 1215 and 1225, through the elongated flexible wire 1210, and from and to a measurement device (not shown). For example, according to one embodiment where the multisite sensor 1200 comprises a pulse oximetry sensor, the sensor element 1215 may comprise circuitry similar to the emitter 306 and the sensor element 1225 may comprise circuitry similar to the photodetector 307. In such an exemplary case, the electrical connector 308 provides electrical communication from the emitter 306 and the photodetector 307, to, for example, an oximeter.

According to the embodiment shown in FIG. 12, the multisite sensor 1200 comprises the neck 1205 and the elongated flexible wire 1210, thereby advantageously providing for convenient positioning of each of the sensor elements 1215 and 1225.

The embodiment shown in FIG. 12 also illustrates the positioning members 1220 and 1230. According to one embodiment, the positioning members 1220 and 1230 are adapted to releasably attach to a sensor wrap configured to properly, straightforwardly and accurately position the respective sensor element to a measurement site. According to one embodiment, the positioning members 1220 and 1230 advantageously comprise button-style detents, or projections having flanges, rims, or the like. The positioning members 1220 and 1230 position and hold one mechanical part in relation to another so that the sensor elements 1215 and 1225 can be releasably attached to the sensor wrap, as disclosed further with reference to FIGS. 14–15.

Although embodiments of the multisite sensor 1200 are disclosed herein with reference to a pulse oximetry sensor including the sensor elements 1215 and 1225, a skilled artisan will recognize from the disclosure herein that the multisite sensor 1200 may advantageously comprise one or more sensor elements of a number of different sensor types. Moreover, the skilled artisan will recognize from the disclosure herein that each of the one or more sensor elements may advantageously include one or more positioning members.

Figure 13:
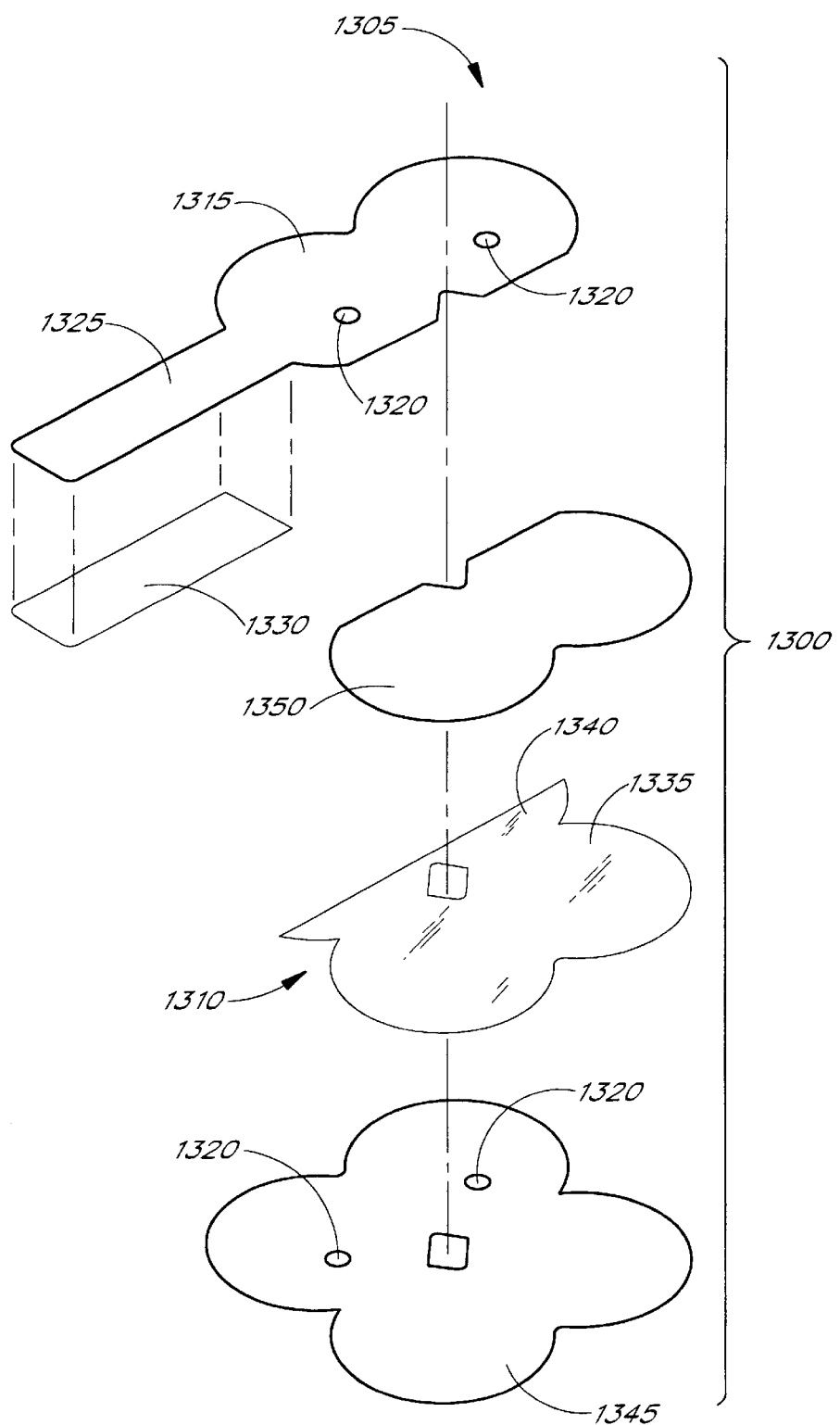
FIG. 13 illustrates an exploded view of a sensor wrap, according to yet another embodiment of the invention.

FIG. 13 illustrates an exploded view of a sensor wrap 1300 according to aspects of yet another embodiment of the invention. As shown in FIG. 13, the sensor wrap 1300 includes a outer layer 1305 and an inner layer 1310. According to one embodiment, the outer layer 1305 may advantageously comprise a foam tape such as that commercially used in a wide variety of medical securing mechanisms, including popular adhesive bandages. A skilled artisan will recognize from the disclosure herein that the outer layer 1305 may comprise other materials having sufficient durability and moldability suitable for forming the ambient-facing portion of the sensor wrap 1300.

FIG. 13 also shows the outer layer 1305 comprises a positioning portion 1315, one or more positioning apertures 1320 and a securing wrap 1325. According to one embodiment, the positioning portion 1315 comprises two substantially oval portions connected to form a generally-figure-eight-like shape having one side at least partially flattened. According to one embodiment, the securing wrap 1325 extends from a side of the positioning portion 1315 and comprises an elongated arm adapted to advantageously wrap around a wide variety of measurement sites, thereby advantageously and properly securing various sensor elements thereto. One embodiment of the securing wrap 1325 uses adhesive coated on one side to secure the sensor wrap 1300 to the measurement site. Accordingly, the securing wrap 1325 may advantageously include a release liner 1330 which covers the adhesive until the sensor wrap 1300 is ready to be applied to a measurement site. A skilled artisan will recognize from the disclosure herein that the release liner 1330 may comprises a wide variety of commercial forms from a wide variety of vendors.

The embodiment shown in FIG. 13 also includes two positioning apertures 1320 each placed approximately in the middle of one of the foregoing substantially oval portions of the positioning portion 1315. According to one embodiment, the positioning apertures 1320 are sized to releasably connect to the positioning members 1220 and 1230 of the multisite sensor 1200 disclosed with reference to FIG. 12. Moreover, in an embodiment where the positioning portion 1315 includes an adhesive side, the positioning members 1220 and 1230 snap into the positioning apertures 1320 of the sensor wrap 1300 and the adhesive of the positioning portion 1315 helps to secure the position and orientation of the sensor elements 1215 and 1225 within the sensor wrap 1300.

FIG. 13 also illustrates the inner layer 1310 of the sensor wrap 1300. According to one embodiment, the inner layer 1310 comprises a foldable side 1335 and an attached side 1340. As shown in FIG. 13, the foldable side 1335 comprises two substantially oval portions connected to form a generally-figure-eight-like shape substantially mirroring the shape of the positioning portion 1315 of the outer layer 1305. According to one embodiment, the foldable side 1335 is advantageously shaped to fold over and substantially match the positioning portion 1315 of the outer layer 1305, as disclosed further with reference to FIGS. 14–15.

According to another embodiment, the attached side 1340 comprises an extension of one edge of the foldable side 1335 appropriately shaped to attach to the positioning portion 1315 of the outer layer 1305. For example, the attached side 1340 may advantageously comprise an extension just sufficient enough to secure the foldable side 1335 to the outer layer 1305. There are at least several advantages in employment of a smaller extension as the foldable side 1335. For example, the extension uses less tape, and is therefore less expensive to manufacture on a per sensor wrap basis. Moreover, according to embodiments including adhesives applied to one or more sides of the foldable side 1335, removal of the sensor elements 1215 and 1225 for reuse is easier when the outer layer 1310 is not affixed to itself in and around the sensor elements 1215 and 1225.

On the other hand, another embodiment of the attached side 1340 may comprise an extension shaped substantially the same as the outer layer 1305, thereby fully attaching as a top layer of the same. According to this embodiment, the inner layer 1305 may advantageously include the positioning apertures 1320.

Although requiring more tape on a per sensor wrap basis, there are at least several advantages in employment of the larger extension as the foldable side 1335. For example, the smaller extensions sometimes use more complex alignment equipment during the assembly of the sensor wrap 1300, while the larger extensions can often take advantage of less expensive and more straightforward alignment equipment. Moreover, the larger extension can more securely affix the sensor elements 1215 and 1225 within the sensor wrap 1300.

A skilled artisan will recognize from the disclosure herein that the attached side 1340 of the inner layer 1310 may advantageously vary from a very small, even tabbed shape, to matching the shape of the outer layer 1305. The determination of the size of the attached side 1340 can be made to balance or exploit one or more of the advantageous aspects disclosed above, such as, for example, the cost per sensor wrap or complexity of the alignment equipment.

According to one embodiment, at least the foldable side 1335 of the inner layer 1310 may comprise a substantially transparent applicator tape having adhesive on one or both sides. The substantially transparent applicator tape including adhesive is advantageous for a number of reasons. For example, when the foldable side 1335 of the inner layer 1310 is folded over the sensor elements 1215 and 1225, the foldable side 1335 may advantageously removably adhere to the same. Moreover, as discussed in the foregoing, the inner layer 1310 folds over the sensor elements 1215 and 1225 on the measurement site-facing side of the sensor wrap 1300. Thus, according to one embodiment, the transparent tape will not harmfully interfere with the emission and detection of light by the sensor elements 1215 and 1225. In addition, adhesive on both sides of the foldable side 1335 of the inner layer 1310 may advantageously adhere directly to the measurement site.

FIG. 13 also shows the inner layer 1310 having release liners 1345 and 1350 to cover each side of the inner layer 1310. According to one embodiment, the release liner 1345 covers the inner layer 1310 and the adhesive side of the positioning portion 1315 of the outer layer 1305 until encapsulating of the sensor elements 1215 and 1225. According to another embodiment, the release liner 1350 covers the other side of the inner layer 1310 until application of the sensor wrap 1300 to a measurement site.

According to one embodiment, the sensor wrap 1300 may advantageously be manufactured as two elements, such as, for example, the outer layer 1305 and the inner layer 1310. In such embodiments, each element may include additional release liners covering exposed adhesives of the same. For example, the attached side 1340 may advantageously include a release liner approximately adjacent to release liner 1350, while the positioning portion 1315 may include a release liner approximately adjacent to release liner 1330. The foregoing release liners can then be removed during assembly, thereby allowing the inner layer 1310 to sufficiently attach to the outer layer 1305. On the other hand, a skilled artisan will recognize from the disclosure herein that the sensor wrap 1300 can be manufactured as a single element, thereby likely voiding the need for the additional release liners.

Figure 14:
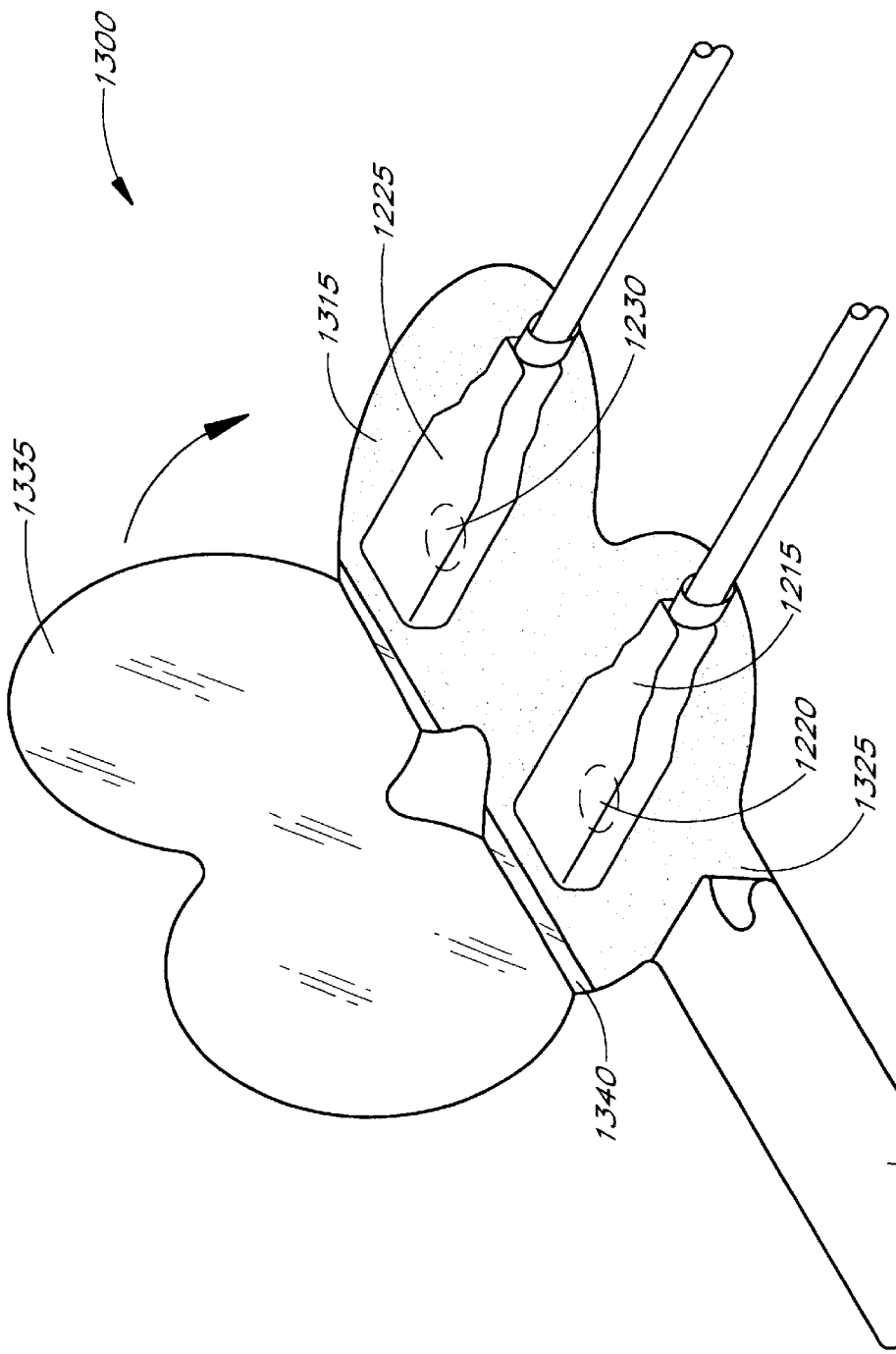
FIG. 14 illustrates a perspective view of the assembly of the sensor wrap of FIG. 13 encapsulating sensor elements of the multisite sensor of FIG. 12, according to aspects of yet another embodiment of the invention.

FIG. 14 illustrates a perspective view of the assembly of the sensor wrap 1300 of FIG. 13 encapsulating the sensor elements 1215 and 1225 of the multisite sensor 1200 of FIG. 12, according to aspects of yet another embodiment of the invention. According to the embodiment shown in FIG. 14, to assemble the sensor wrap 1300, the release liner 1345 is removed from the foldable side 1335 of the inner layer 1310 and the adhesive side of the positioning portion 1315 of the outer layer 1305. FIG. 14 illustrates the adhesive with dots. Once the adhesive is exposed, the sensor elements 1215 and 1225 are positioned on the positioning portion 1315 using the positioning apertures 1320 and positioning members 1220 and 1230 shown in phantom. According to this embodiment, the positioning portion 1315 adheres to the sensor elements 1215 and 1225 to substantially fix their position and orientation within the sensor wrap 1300. As shown in FIG. 14, the transparent foldable side 1335 is then folded over the sensor elements 1215 and 1225, thereby securing their positions within the sensor wrap 1300. For example, the folded side 1335 releasably secures the vertical and horizontal spatial relationship between the sensor elements 1215 and 1225 within the sensor wrap 1300 before application thereof to a measurement site.

A skilled artisan will recognize from the disclosure herein that the positioning members 1220 and 1230 may advantageously be adapted to sufficiently fix the position and orientation of the sensor elements 1215 and 1225, in place of or in addition to the adhesive disclosed in the foregoing. In addition, the skilled artisan will recognize from the disclosure herein other sensor types or other sensor wrap shapes, where the foldable aspects of the foregoing embodiments may be used to create a secure assembled sensor wrap.

Figure 15:
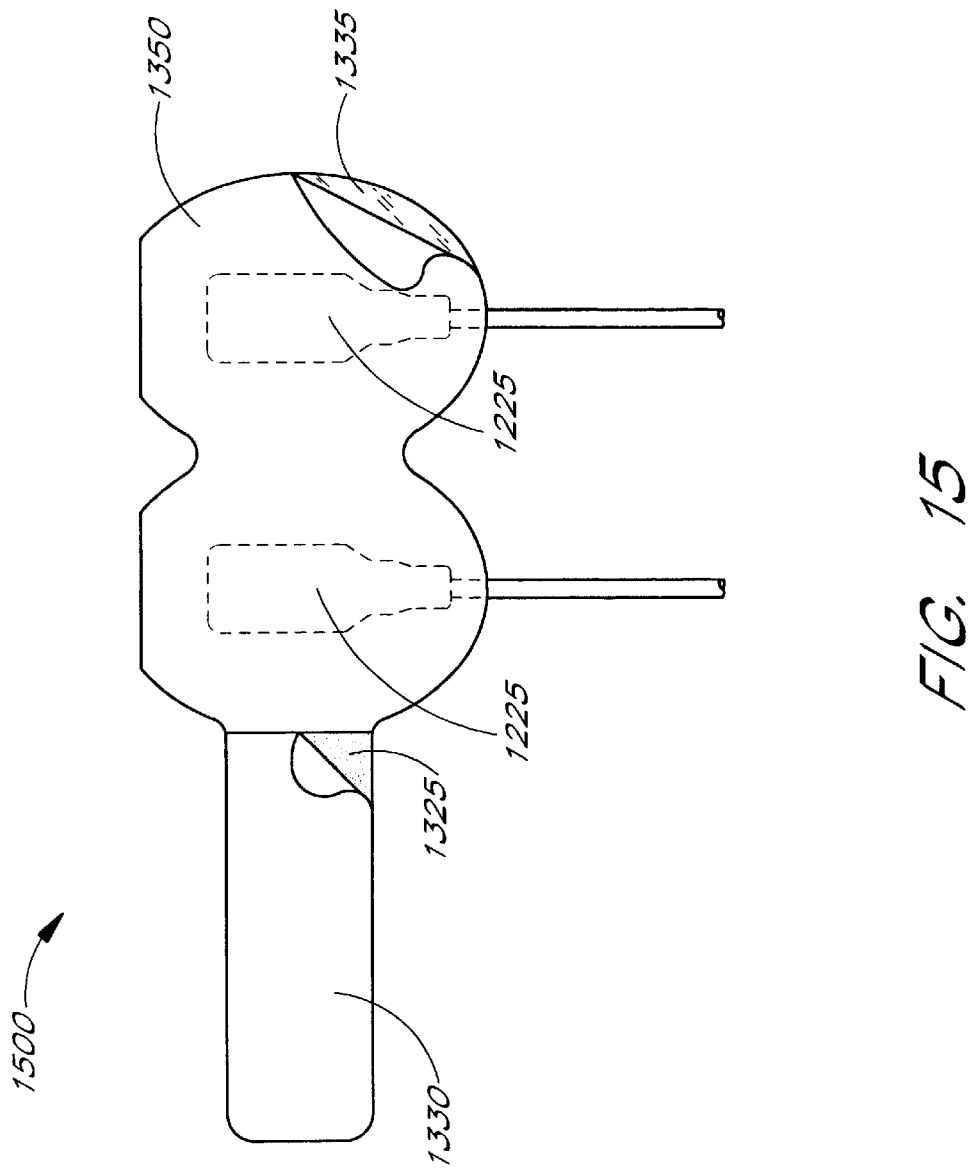
FIG. 15 illustrates a bottom view of an assembled sensor wrap, according to aspects of yet another embodiment of the invention.

FIG. 15 illustrates a bottom view of an assembled sensor wrap 1500, according to aspects of an embodiment of the invention. As shown in FIG. 15, the foldable side 1335 of the inner layer 1310 covers the sensor elements 1215 and 1225, shown in phantom. In addition, FIG. 15 illustrates the assembled sensor wrap 1500 including the release liner 1330 and the release liner 1350 still covering the adhesives of the sensor wrap 1300. Thus, the assembled sensor wrap 1500 advantageously provides for the proper positioning of reusable circuitry within a disposable wrap without exposing the measurement site attaching adhesives to the environment. Because the assembled sensor wrap 1500 still includes the release liners 1330 and 1350, the assembled sensor wrap 1500 need not be immediately used. Thus, the assembled sensor wrap 1500 advantageously allows for wrap assembly before the need for actual use arises.

According to one embodiment, the assembled sensor wrap 1500 is applied to a measurement site, such as a finger, by first removing the release liners 1330 and 1350. Then, the foldable side 1335 of the assembled sensor wrap 1500 is attached to the measurement site and the securing wrap 1325 is wrapped around the same, thereby accurately and appropriately placing the sensor elements 1215 and 1220 in relation to one another around the measurement site.

When the time arrives to dispose of the sensor wrap 1300, the reusable circuitry, i.e., the sensor elements 1215 and 1225, is removed from the sensor wrap 1300 and the sensor wrap 1300 is discarded. As with embodiments disclosed in the foregoing, the reusable circuitry may be optionally sterilized and then reinserted within a new sensor wrap 1300.

Although the embodiments shown in FIGS. 14 and 15 employ apertures 1320 and positioning members 1220 and 1230 to position the sensor elements 1215 and 1225, a skilled artisan will recognize from the disclosure herein other releasable attachment mechanisms that may be used in addition to, or as an alternative of the foregoing mechanism, such as, for example, adhesives, hook or slidable members, hook-and-loop attachment mechanisms, friction-fit or other detents, or the like.

Aspects of the embodiments disclosed with respect to FIGS. 12–15 illustrate a sensor wrap 1300 including a foldable applicator or side 1335 which advantageously keeps the reusable sensor elements 1215 and 1225 isolated from patient cross-contamination. For example, the foldable side 1335 substantially covers the entirety of the sensor elements 1215 and 1225. Moreover, employment of the sensor wrap 1300 smoothes the topographical transition from the sensor elements 1215 and 1225, to the inner layer 1310, thereby reducing pressure points and the possibility of pressure necrosis occurring in the measurement site. Moreover, according to one embodiment, proper application of the sensor wrap 1300 advantageously places the tops of the ovals in a position to be folded over the measurement site, thereby reducing the amount of ambient light available to the sensor element 1225.

Figure 16B:
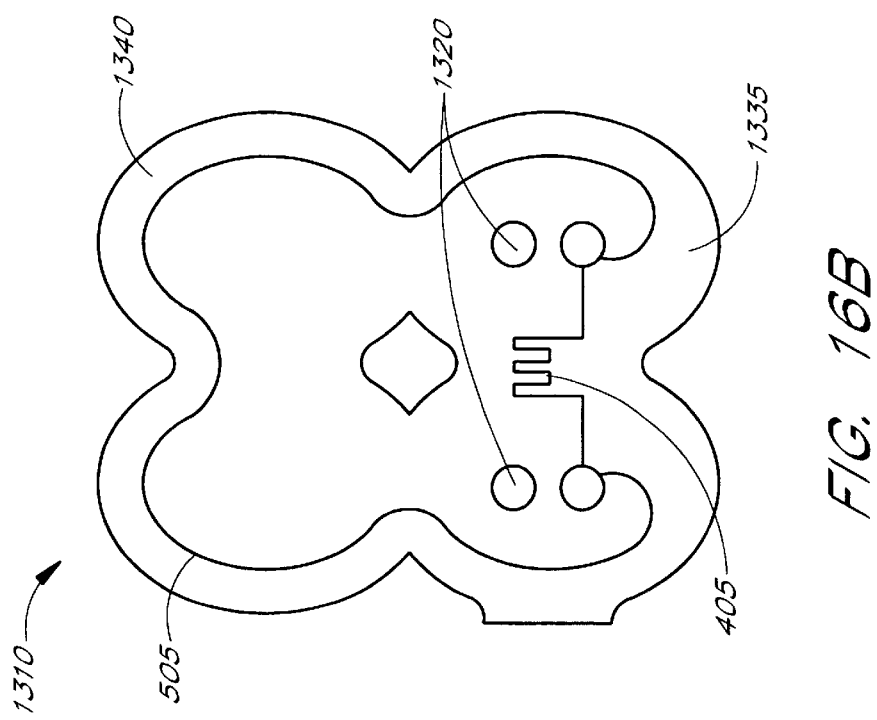
FIG. 16B illustrates a bottom view of a clear tape layer incorporating a breakable conductor and an information element, according to aspects of yet another embodiment of the invention.
Figure 16A:
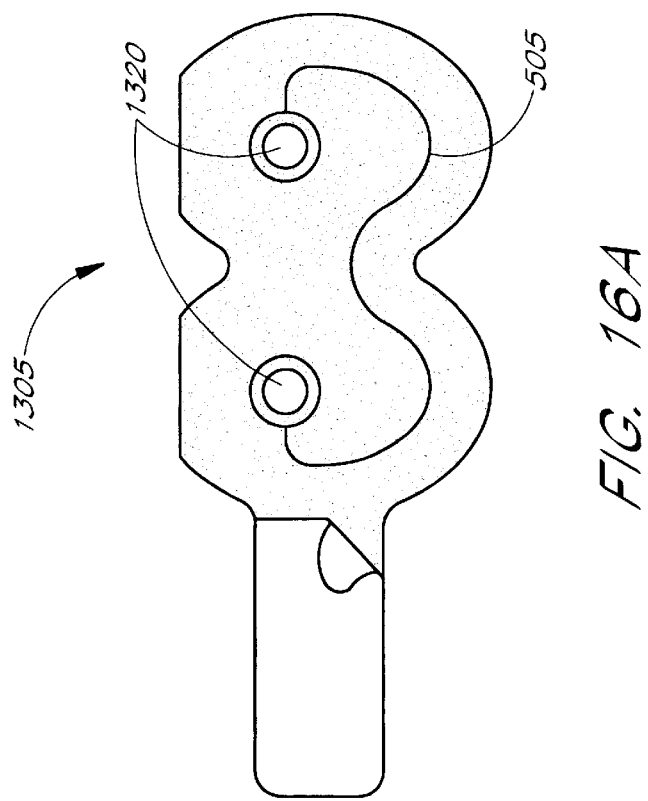
FIG. 16A illustrates a bottom view of the foam tape layer of FIG. 13 incorporating a breakable conductor, according to aspects of yet another embodiment of the invention.

Although the foregoing invention has been described in terms of certain preferred embodiments, other embodiments will be apparent to those of ordinary skill in the art. For example, aspects of FIGS. 3–11 may be combined with those of FIGS. 12–15. For example, as shown in FIGS. 16A and 16B, the breakable conductor 505 of FIG. 5, the information element of FIG. 4, or both, may advantageously be incorporated into one of the layers 1305 or 1310 in a wide number of potential trace shapes and configurations in a wide number of tape shapes. For example, FIG. 16A illustrates the breakable conductor 505 incorporated into the foam tape layer 1305 via contacts surrounding the positioning apertures 1320. Alternatively, FIG. 16B illustrates an embodiment wherein the inner layer 1310 comprises an elongated side 1340 sized similar to the outer layer 1305. As shown in FIG. 16B, contacts connect the breakable conductor 505 and the information element 405 to the sensor elements 1215 and 1225. As disclosed in the foregoing, the breakable conductor 505, the information element, or both, advantageously add the ability to control overuse, misuse, and the like for the various sensor wraps disclosed herein.

Figure 17A:
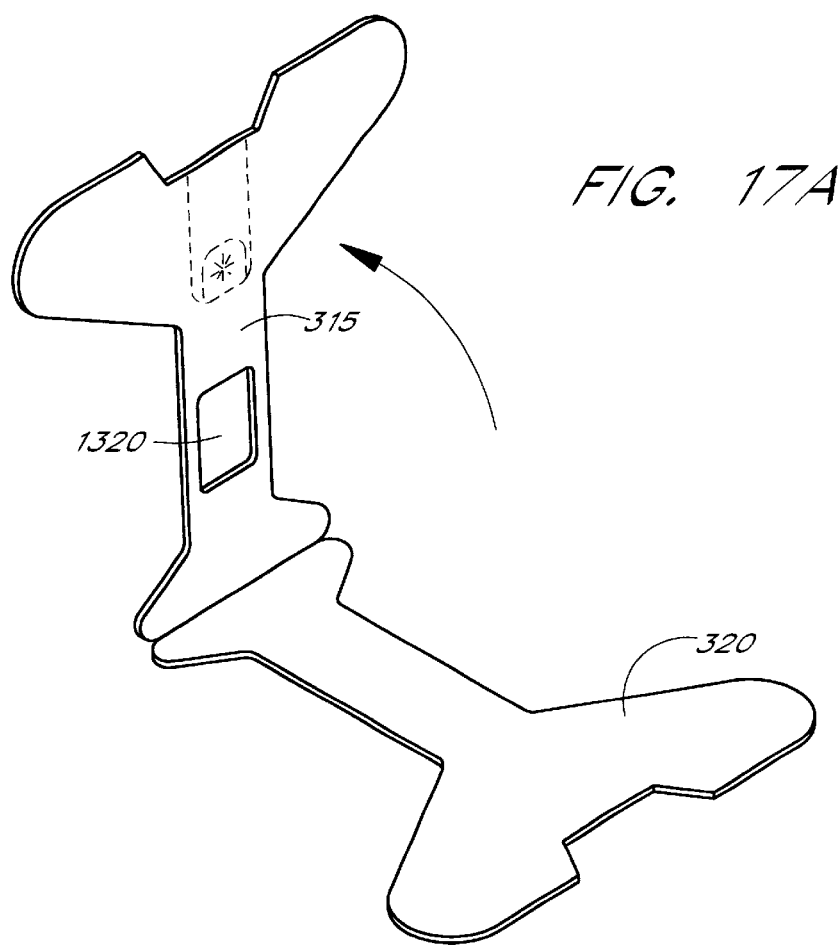
FIGS. 17–20 illustrate perspective views of other embodiments of a foldable sensor wrap.
Figure 17B:
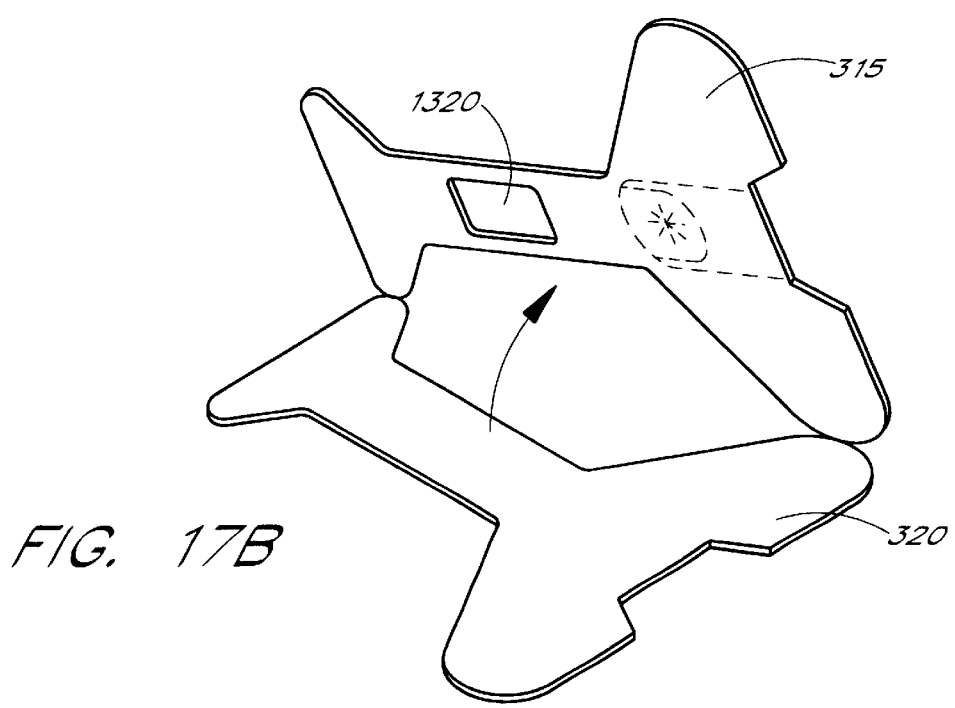
Figure 18A:
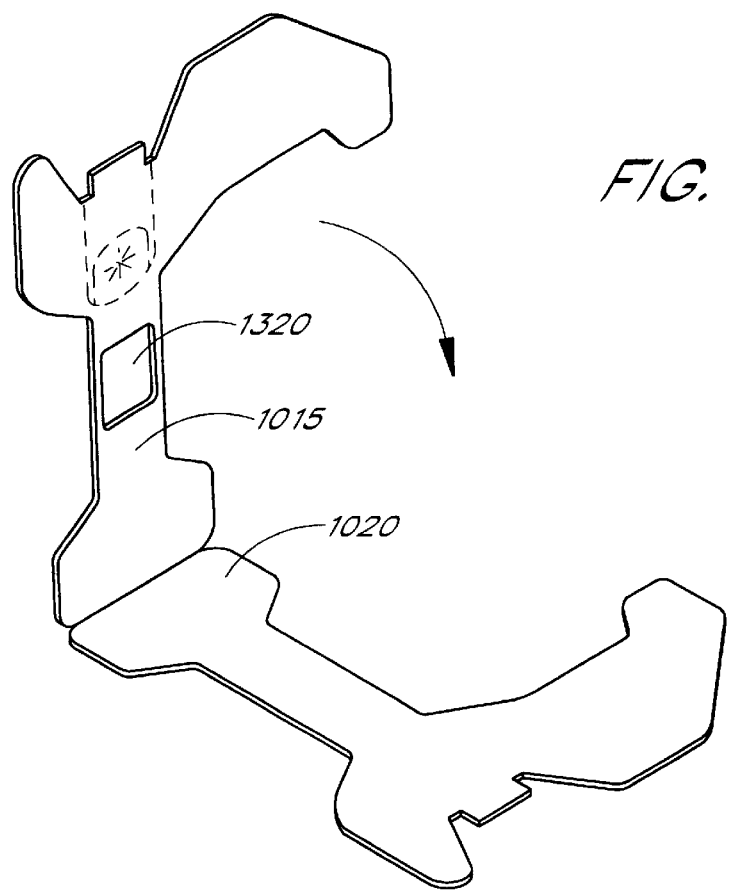
Figure 18B:
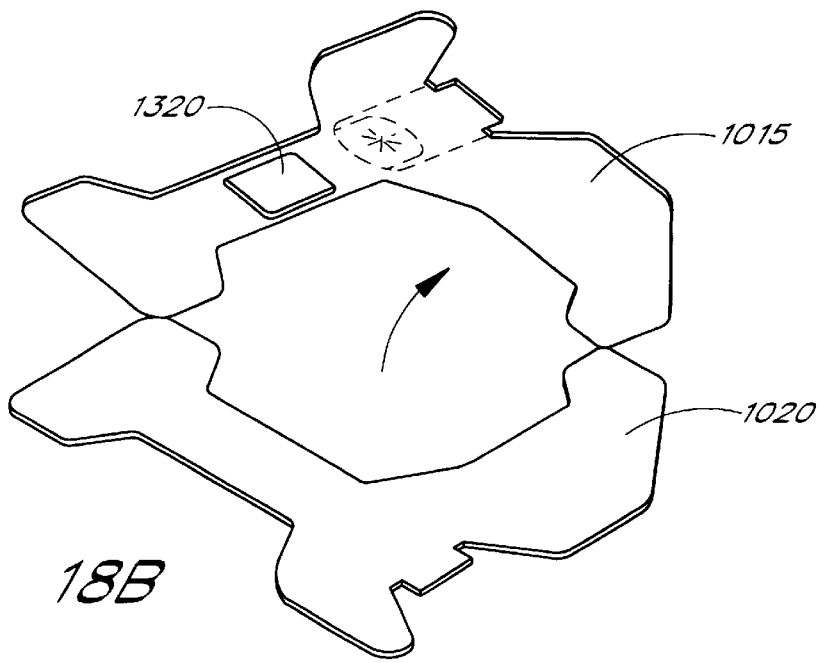
Figure 19A:
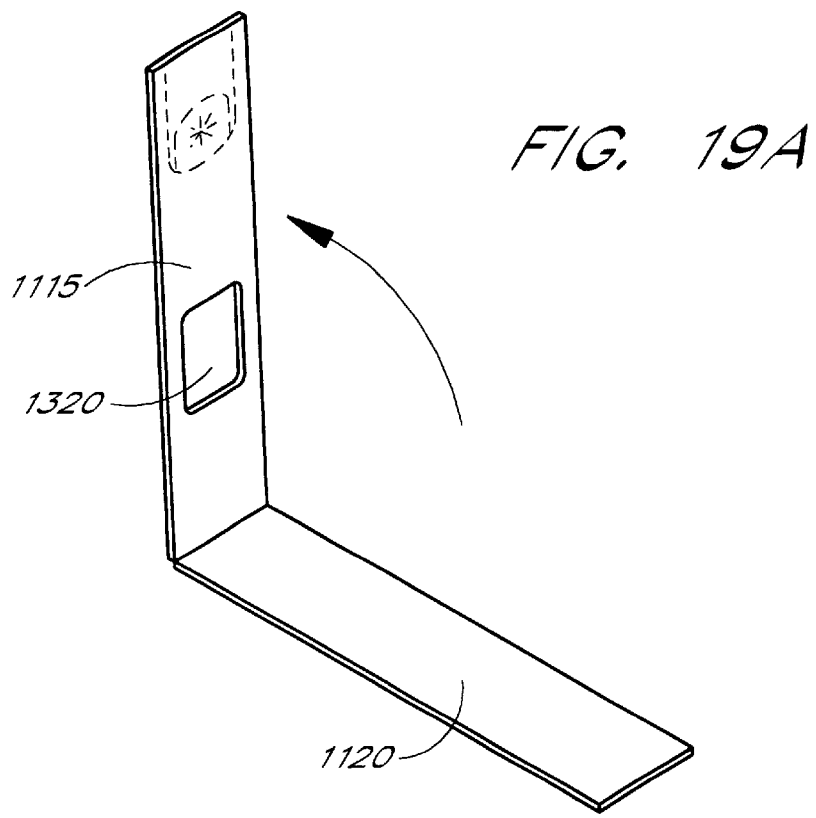
Figure 19B:
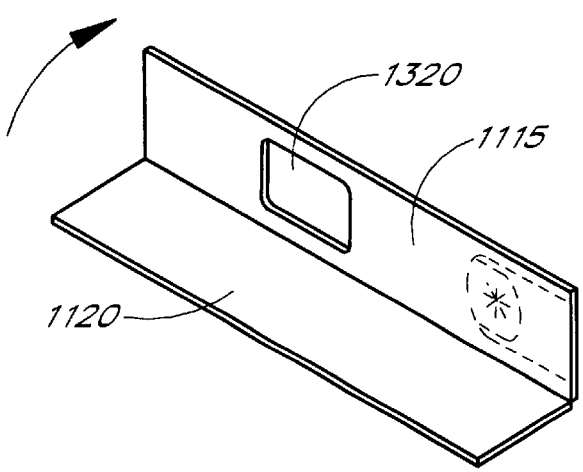

Additionally, the skilled artisan will recognize from the disclosure herein a wide number of shapes of the sensor wrap 1300, the outer layer 1305, the inner layer 1310, the foldable side 1335, the securing wrap 1325, or combinations thereof. Also, select aspects of FIGS. 12–16 may advantageously be combined with the shapes of the disposable tape disclosed with reference to FIGS. 3, and 9–11. For example, FIGS. 17–19 illustrate perspective views of other embodiments of sensor wraps having foldable sides 320, 1020, and 1120, according to aspects of other embodiments of the invention. Similar to the disclosure of FIGS. 12–16, the measurement site-facing side of the sensor wraps of FIGS. 17–19 may advantageously comprise transparent material, may have aperture openings, may have an adhesive coatings on each side, or the like. Moreover, the sensor wraps of FIGS. 17–19 may advantageously incorporate one or more positioning apertures 1320 for sensor components having one or more positioning members, similar to those disclosed with reference to FIGS. 10–11.

Figure 20B:
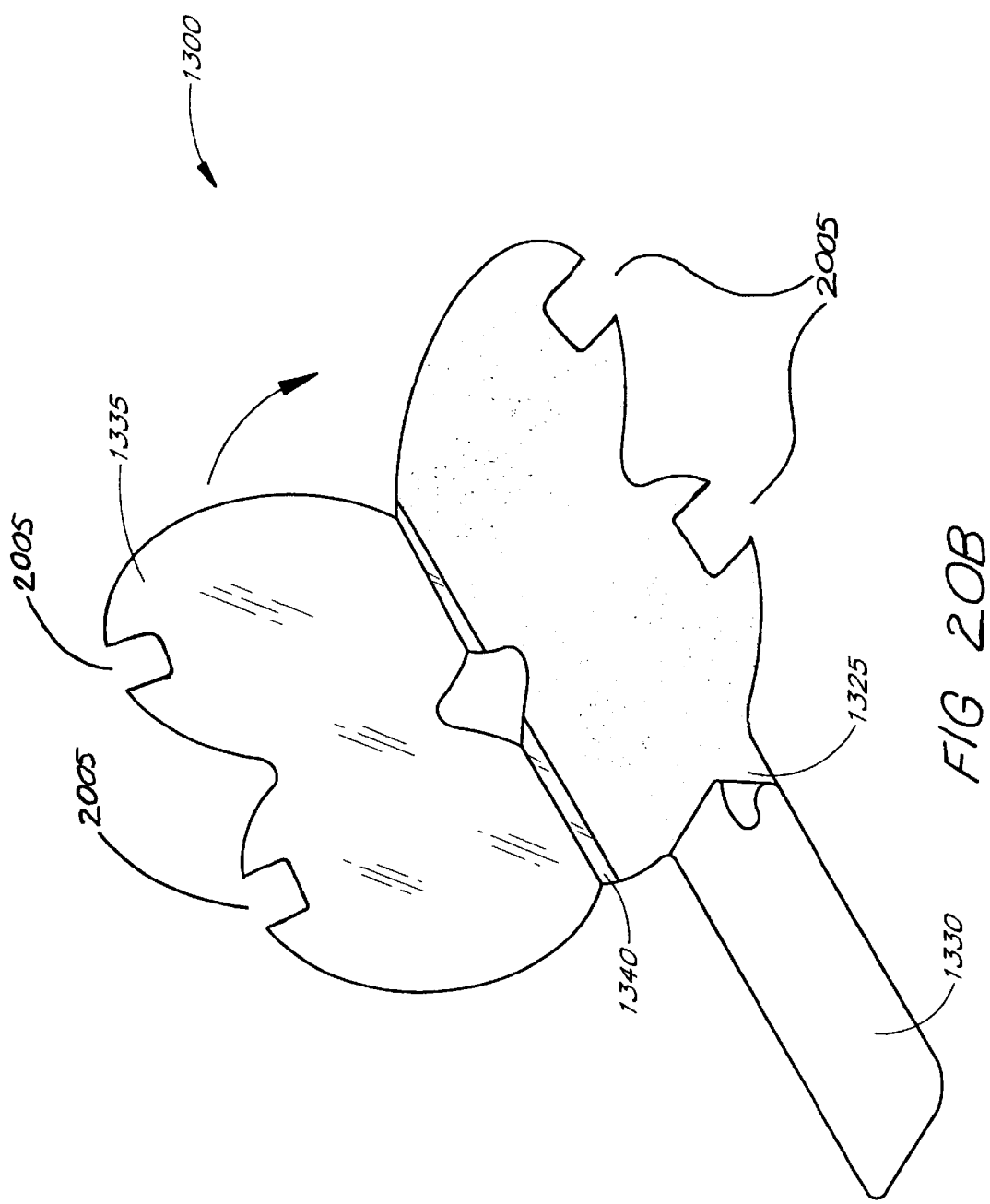

A skilled artisan will also recognize from the disclosure herein that the foregoing sensor wraps of FIGS. 13 and 16–19 can be configured without positioning apertures to straightforwardly and accurately position sensor elements without positioning members within the sensor wraps. For example, FIGS. 20A and 20B illustrate sensor wraps 1300 having positioning indicators 2005 directing an assembler as to where to place sensor elements, such as an emitter, a detector, other reusable circuitry, or the like, within the sensor wraps. For example, FIG. 20A shows the positioning indicators 2005 as solid ink outlines indicating where the elements are to be placed. As disclosed in the foregoing, once positioned within the sensor wrap using the positioning indicators 2005, the foldable side 1335 of the sensor wrap can be folded over the sensor elements thereby substantially fixing their position within the wrap. A skilled artisan will recognize that the positioning indicators 2005 can be broken lines, phantom lines, scores on the tape, or the like. FIG. 20B shows yet another embodiment where the indicators 2005 comprise notches, which can be stamped, scored, or the like, from one or more sides of the sensor wrap. Similar to FIG. 20A, an assembler can use the notches as a guide in placing the sensor elements within the sensor wrap.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. A sensor wrap for removably securing an emitter and detector circuit assembly of a pulse oximetry sensor to body tissue of pulsing blood, the sensor wrap comprising:

a center tape portion configured to position an assembled reusable emitter and detector circuit assembly of a pulse oximetry sensor;

a securing tape portion extending from the center tape portion and configured to removably secure the sensor wrap proximate to body tissue carrying pulsing blood; and a foldable portion including an attached side and a free side, wherein at least a portion of the attached side is attached to the center tape portion and the free side is configured to, before application of the sensor wrap to the body tissue, fold over the emitter and detector circuit assembly when the emitter and detector circuit assembly are positioned within the center tape portion to affix the emitter and detector circuit assembly between the center tape portion and the foldable portion, thereby forming an assembled sensor capable of removably securing the emitter and detector circuit assembly proximate the body tissue carrying the pulsing blood.

2. The sensor wrap of claim 1, wherein the foldable portion comprises a transparent layer.

3. The sensor wrap of claim 1, wherein the center tape portion includes apertures configured to receive positioning portions of the emitter and detector circuit assembly.

4. The sensor wrap of claim 1, further comprising a disposable information element within at least one of the center tape portion and the foldable portion, wherein the information element is configured to electrically connect to an emitter of the emitter and detector circuit assembly when the emitter and detector circuit assembly is positioned within the sensor wrap.

5. The sensor wrap of claim 1, further comprising a breakable conductive trace within at least one of the center tape portion and the foldable portion, wherein the breakable conductive trace is configured to electrically disconnect an emitter of the emitter and detector circuit assembly when the emitter and detector circuit assembly is positioned within the sensor wrap and the breakable conductive trace is broken.

6. The sensor wrap of claim 1, wherein the center tape portion is configured to position the assembled reusable emitter and detector circuit assembly comprising a Y-type sensor.

7. The sensor wrap of claim 1, wherein the center tape portion is configured to position the assembled reusable emitter and detector circuit assembly comprising a flexible circuit.

8. A sensor wrap including a foldable tape for positioning elements of a sensor within the sensor wrap before application of the sensor wrap to a measurement site thereby properly positioning the elements of the sensor with respect to one another, and eventually with respect to the measurement site on body tissue carrying pulsing blood, the sensor wrap comprising:

a base tape comprising a positioning portion which receives an assembled circuit assembly including an assembled emitter and an assembled detector;

a foldable tape attached to the base tape, wherein the foldable tape folds over the assembled circuit assembly before application of the sensor wrap to a measurement site, thereby removably securing the assembled circuit assembly within the sensor wrap; and a fastener which removably secures the sensor wrap to the measurement site.

9. The sensor wrap of claim 8, wherein the base tape further comprises a breakable conductor.

10. The sensor wrap of claim 8, wherein the foldable tape further comprises a breakable conductor.

11. The sensor wrap of claim 8, wherein the base tape further comprises an information element.

12. The sensor wrap of claim 8, wherein the foldable tape further comprises an information element.

13. The sensor wrap of claim 8, wherein the base tape comprises a figure eight-like shape.

14. The sensor wrap of claim 8, wherein the foldable tape comprises a figure eight-like shape attached at a side.

15. The sensor wrap of claim 8, wherein the fastener comprises an elongated arm extending from one of the base tape and the foldable tape.

16. The sensor wrap of claim 8, wherein the positioning portion comprises at least one aperture.

17. The sensor wrap of claim 8, wherein the base tape comprises a boot-like shape, and wherein the fastener comprises a toe portion of the boot-like shape.

18. The sensor wrap of claim 8, wherein the foldable tape comprises a boot-like shape, and wherein the fastener comprises a toe portion of the boot-like shape.

19. The sensor wrap of claim 8, wherein the base tape comprises a substantially rectangular shape.

20. The sensor wrap of claim 8, wherein the foldable tape comprises a substantially rectangular shape.

21. The sensor wrap of claim 8, wherein the base tape comprises an elongated center section connecting front and rear flaps, and wherein the fastener comprises the front and rear flaps.

22. The sensor wrap of claim 8, wherein the foldable tape comprises an elongated center section connecting front and rear flaps, and wherein the fastener comprises the front and rear flaps.

23. The sensor wrap of claim 8, wherein the foldable tape is transparent.

24. The sensor wrap of claim 8, wherein the base tape receives the assembled circuit assembly comprising a Y-type sensor.

25. The sensor wrap of claim 8, wherein the base tape receives the assembled circuit assembly comprising a flexible circuit.

26. A method of manufacturing a sensor wrap, the method comprising:

forming a base tape including at least one positioning element configured to position an assembled reusable sensor elements on the base tape;

forming a foldable tape including adhesive on at least one side and configured to fold over the sensor elements positioned on the base tape before application of the sensor wrap to a measurement site, thereby removably securing the sensor elements within the sensor wrap; and connecting the foldable tape to the base tape.

27. The method of claim 26, further comprising attaching release liners to exposed adhesive.

28. The method of claim 26, wherein the act of connecting the foldable tape to the base tape further comprises:

removing a release liner from a portion of the foldable tape; and attaching the portion to the base tape.

29. The method of claim 26, wherein the act of connecting the foldable tape to the base tape further comprises:

removing a release liner from a portion of the base tape; and attaching the portion to the foldable tape.

30. The method of claim 26, wherein the forming the base tape further comprises forming a base tape configured to position a Y-type sensor.

31. The method of claim 26, wherein the forming the base tape further comprises forming a base tape configured to position a flexible circuit.

32. A method of attaching a sensor having reusable and disposable portions, the method comprising:

removing a release liner on a center portion of a disposable positioning tape;

attaching reusable fully-assembled elements of a sensor to the center portion; and folding a foldable portion over the reusable elements of the sensor before application of the disposable positioning tape to a measurement site, thereby securing the reusable elements of the sensor within the center portion.

33. The method of claim 32, wherein the attaching reusable elements comprises aligning positioning elements of the sensor with positioning elements within the center portion.

34. The method of claim 33, wherein the positioning element within the center portion comprises an aperture.

35. The method of claim 32, wherein at least one of the attaching the reusable elements and the folding the foldable portion includes electrically connecting an information element to one of the reusable elements of the sensor.

36. The method of claim 32, wherein at least one of the attaching the reusable elements and the folding the foldable portion includes electrically connecting a breakable conductor to one of the reusable elements of the sensor.

37. The method of claim 32, further comprising:

removing release liners from other portions of the disposable positioning tape; and affixing the disposable positioning tape, with the reusable sensor elements, to a measurement site.

38. The method of claim 32, wherein the attaching reusable elements further comprises attaching a Y-type sensor.

39. The method of claim 32, wherein the attaching reusable elements further comprises attaching a flexible circuit.

* * * * *